(12) United States Patent
Brucheimer et al.

(10) Patent No.: US 7,749,244 B2
(45) Date of Patent: Jul. 6, 2010

(54) INTRAVASCULAR DEVICES, RETRIEVAL SYSTEMS, AND CORRESPONDING METHODS

(75) Inventors: Elchanan Brucheimer, Zichron Yaakov (IL); Simon Bruckheimer, London (GB); Issack Tavori, Herzlia (IL); Gil Naor, Ramot Hashavim (IL); Danny Kinarty, Haifa (IL)

(73) Assignee: Rafael Medical Technologies Inc., Dover, DE (US)

( * ) Notice: Subject to any disclaimer, the term of this patent is extended or adjusted under 35 U.S.C. 154(b) by 882 days.

(21) Appl. No.: 10/488,319

(22) PCT Filed: Sep. 10, 2002

(86) PCT No.: PCT/IL02/00749

§ 371 (c)(1), (2), (4) Date: Mar. 2, 2004

(87) PCT Pub. No.: WO03/022325

PCT Pub. Date: Mar. 20, 2003

(65) Prior Publication Data

US 2004/0186512 A1    Sep. 23, 2004

Related U.S. Application Data

(60) Provisional application No. 60/318,005, filed on Sep. 10, 2001, provisional application No. 60/317,925, filed on Sep. 10, 2001, provisional application No. 60/317,926, filed on Sep. 10, 2001.

(51) Int. Cl.
*A61M 29/00* (2006.01)

(52) U.S. Cl. .................................. 606/200

(58) Field of Classification Search ................. 606/200, 606/198, 108, 195, 151; 604/104; 623/1.36, 623/1.11
See application file for complete search history.

(56) References Cited

U.S. PATENT DOCUMENTS

| 3,952,747 | A | * | 4/1976 | Kimmell, Jr. ................. 606/195 |
| 4,992,454 | A | | 2/1991 | Richardson et al. |
| 5,064,428 | A | * | 11/1991 | Cope et al. ..................... 606/127 |
| 5,944,728 | A | * | 8/1999 | Bates ........................... 606/127 |
| 6,063,933 | A | | 5/2000 | Karimian et al. |

(Continued)

FOREIGN PATENT DOCUMENTS

GB    2276325    9/1994

(Continued)

OTHER PUBLICATIONS

IL Patent Application 143007 (Pending) Filed May 7, 2001 Entitled "Retrievable Intravascular support structures".

*Primary Examiner*—Todd E Manahan
*Assistant Examiner*—Diane Yabut
(74) *Attorney, Agent, or Firm*—Mark M. Friedman

(57) ABSTRACT

A semi-retrievable intravascular filter (100) for deployment within a vessel (108) includes a support structure (104) for deployment around an internal surface of the vessel (108) and a filter structure (102) supported by interconnection with the support structure (104). The filter structure (102) is connected to the support structure (104) so as to be selectively detachable so as to facilitate removal of the filter structure (102) without the support structure (104). Also described are various retrieval systems for retrievable or semi-retrievable intravascular devices, and intravascular filter structures.

8 Claims, 23 Drawing Sheets

U.S. PATENT DOCUMENTS

| | | |
|---|---|---|
| 6,146,404 A | 11/2000 | Kim et al. |
| 6,159,220 A | 12/2000 | Gobron et al. |
| 6,224,612 B1 | 5/2001 | Bates et al. |
| 6,251,122 B1 * | 6/2001 | Tsukernik .................. 606/200 |
| 6,302,895 B1 | 10/2001 | Gobron et al. |
| 6,361,546 B1 * | 3/2002 | Khosravi .................... 606/200 |
| 6,482,222 B1 | 11/2002 | Bruckheimer et al. |
| 6,626,915 B2 * | 9/2003 | Leveillee .................... 606/114 |
| 2002/0042617 A1 * | 4/2002 | Ouchi ........................ 606/127 |

FOREIGN PATENT DOCUMENTS

| | | |
|---|---|---|
| WO | WO96/12448 | 5/1996 |
| WO | WO98/36694 | 8/1998 |
| WO | WO00/16846 | 3/2000 |

* cited by examiner

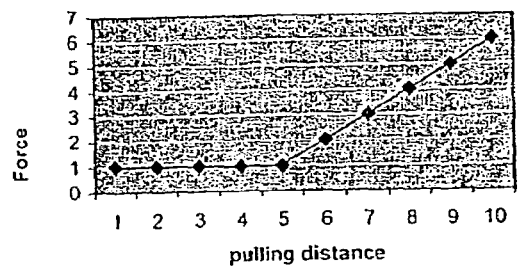
Figure 12B  The Force transmitted through the wire from the proximal end to the filter as the snare catches the filter.
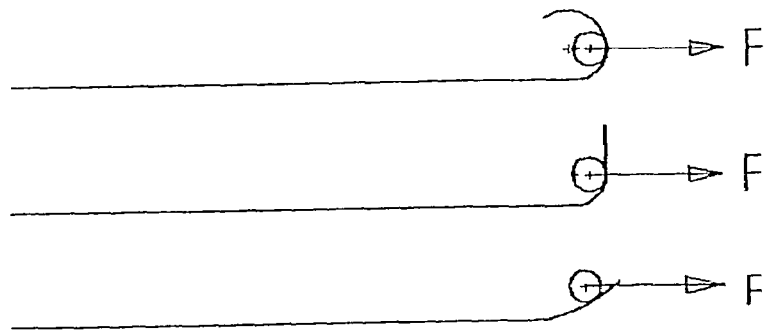
Figure 12C
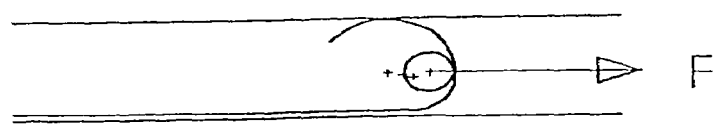
Figure 12D

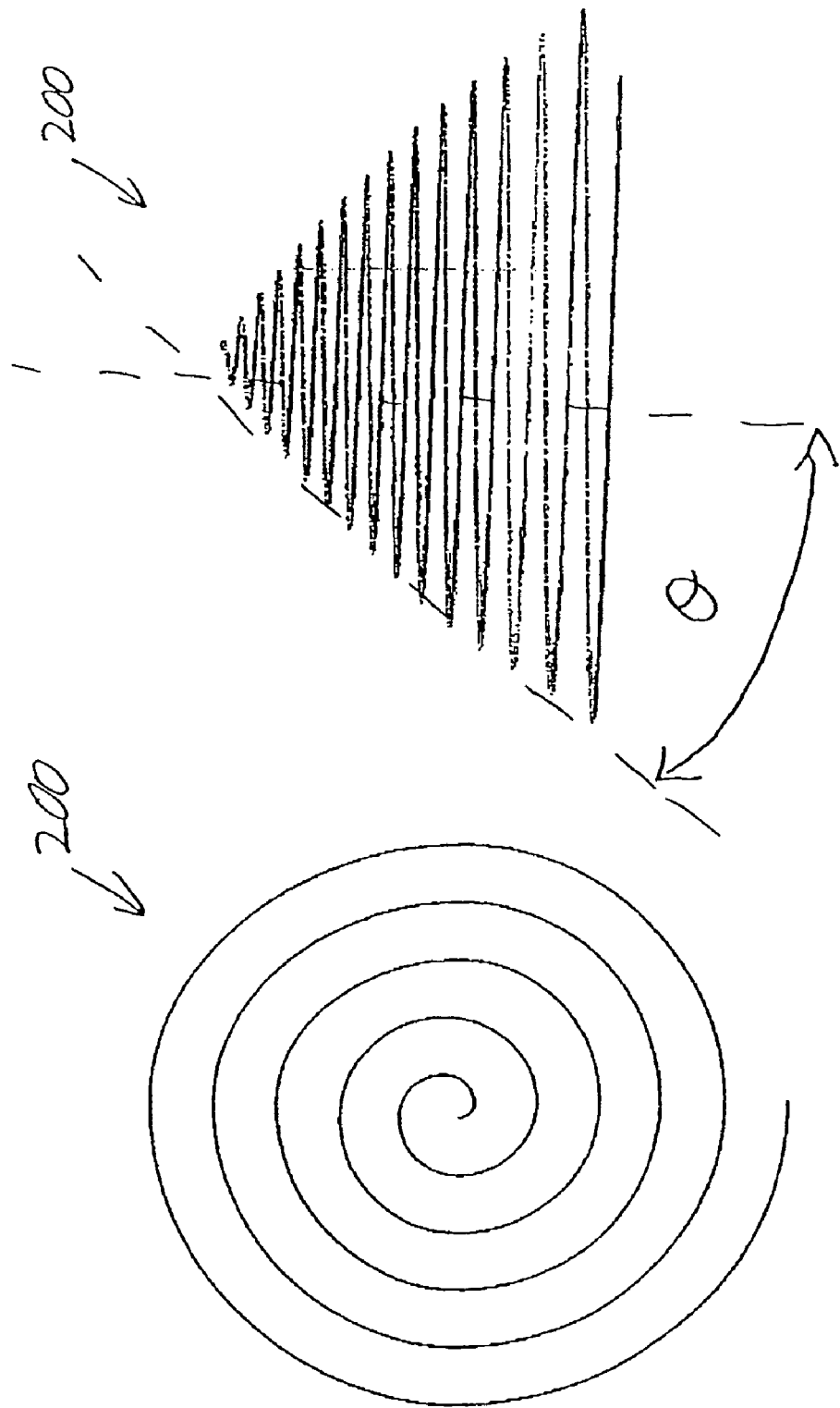

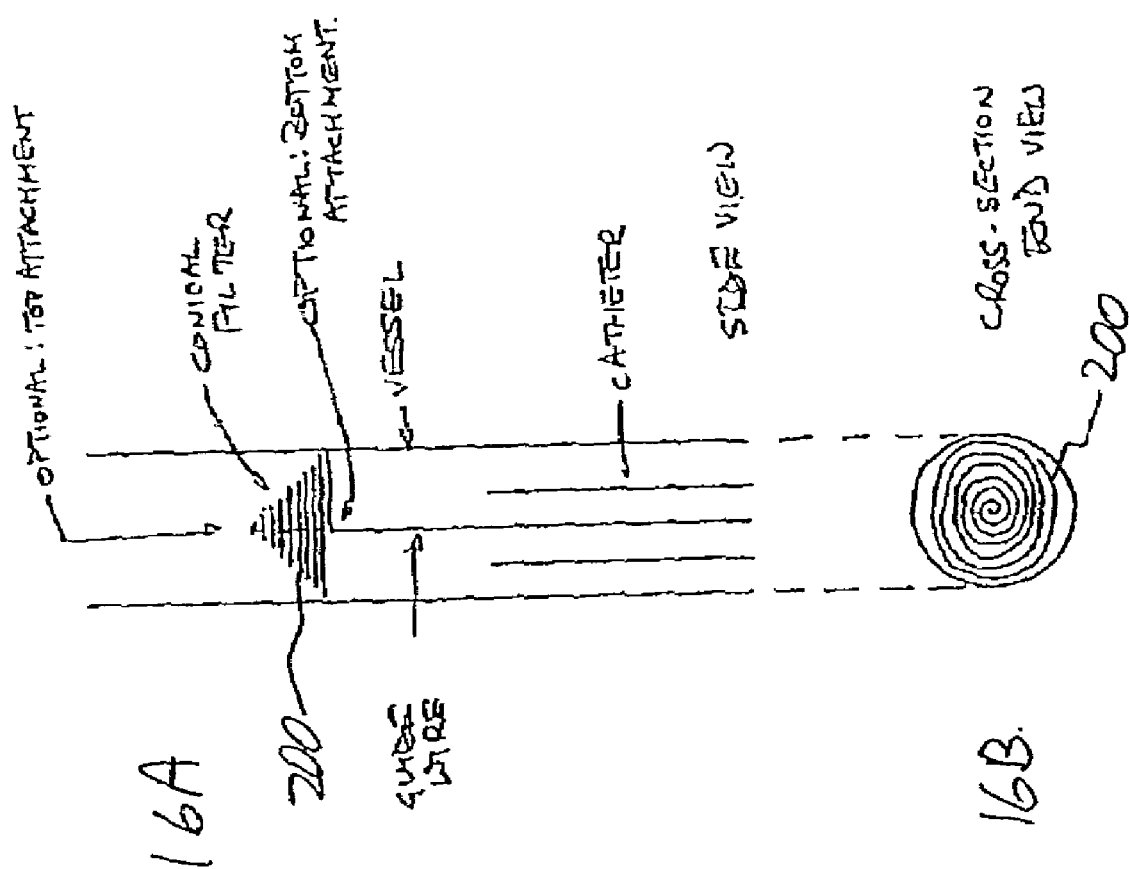

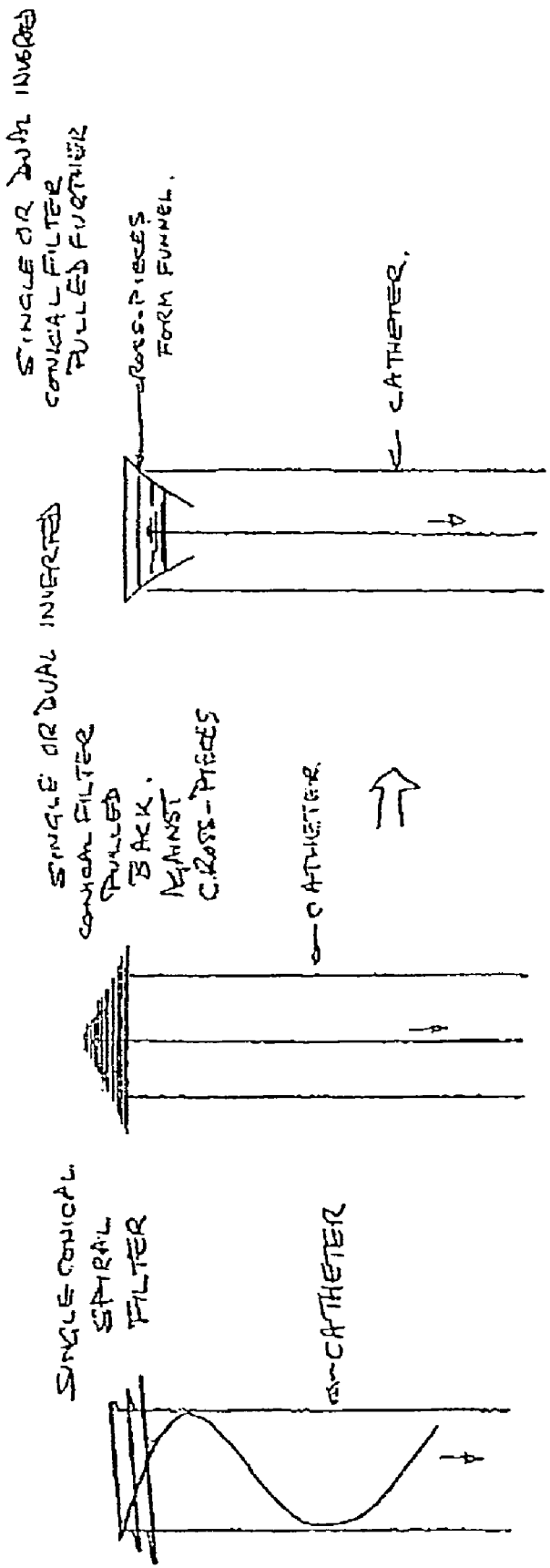

98% reduction, 26 loops, 6 turns

97% reduction, 30 loops, 6 turns 43 loops, 15 turns

INTRAVASCULAR DEVICES, RETRIEVAL SYSTEMS, AND CORRESPONDING METHODS

CROSS REFERENCE TO RELATED APPLICATIONS

This application is the U.S. National stage of International Application No. PCT/IL02/00749 filed on Sep. 10, 2002, published in English, which claims the benefit of U.S. Provisional Application Nos. 60/318,005, 60/317,925, 60/317,926 all filed on Sep. 10, 2001. The entire teachings of the above application(s) are incorporated herein by reference.

FIELD AND BACKGROUND OF THE INVENTION

The present invention relates to intravascular devices and, in particular, it concerns semi-retrievable intravascular devices and corresponding methods. The invention also relates to retrieval systems for retrieving intravascular devices, and filter structures for use in intravascular devices.

Co-pending, co-assigned patent applications: U.S. patent application Ser. No. 09/613,760; PCT Patent Application No. IL00/00553; Israel Patent Application No. 143007; and PCT Patent Application No. IL01/00636, describe various filter configurations which include stabilizing elements (helical and/or ring-like elements) which support an inner filter wire. Since the stabilizing elements have rings which are in contact with the vessel wall, if these devices are used for extended periods, the wires of the stabilizing elements become permanently attached to the vessel wall as endothelium grows over them. Subsequent removal of the device then risks causing significant damage to the vessel.

It would therefore be useful to provide devices and corresponding methods which would facilitate extended use of intravascular devices and then subsequently allow removal of at least the part of the device which causes most obstruction to flow through the vessel while avoiding significant damage to the vessel itself.

Turning now to systems for retrieving previously deployed intravascular devices, the predominant retrieval system is based upon a snare mechanism in which a loop is placed wound part of the device and tightened. This mechanism inherently tends to twist the captured device sideways, thereby rendering it difficult to draw the device into a retrieval catheter unless the catheter is greatly oversized. A further problem with the snare mechanism is the difficulty in positioning the loop around part of the device. This typically requires real time imaging techniques, and even then, can be a difficult and time consuming procedure.

There is therefore a need for a retrieval system which tends to align the captured part of an intravascular device so that it can be drawn into a catheter of dimensions only slightly larger than the diameter of the captured part of the device. It would also be highly advantageous to provide a retrieval system which would allow convenient, or even "blind" retrieval, of an intravascular device without complicated manipulation.

Turning finally to intravascular filter structures, a number of options for implementing intravascular filter structures are described in the above-referenced PCT application. For relatively coarse filtering, such as for large emboli in the inferior vena cava ("IVC"), the structures described therein are highly effective. Where finer filtering is required, for example for distal protection during procedures in the carotid artery, the length of wire required to reliably achieve the required filtering effect increases sharply and is non-optimal.

There is therefore a need for intravascular filter structures, both for tethered use and as part of un-tethered devices, which would achieve finer filtering for a given length of wire:

SUMMARY OF THE INVENTION

The present invention relates to intravascular devices and, in particular, it concerns semi-retrievable intravascular devices and corresponding methods. The invention also relates to retrieval systems for retrieving intravascular devices, and filter structures for use in intravascular devices.

According to the teachings of the present invention there is provided, a semi-retrievable intravascular device for deployment within a vessel comprising: (a) a support structure for deployment around an internal surface of the vessel; (b) a device structure supported by interconnection with the support structure, wherein the device structure is connected to the support structure so as to be selectively detachable so as to facilitate removal of the device structure without the support structure.

According to a further feature of the present invention, the support structure includes: (a) a first substantially closed loop of wire configured to assume a shape lying substantially on a virtual cylinder of given diameter; b) at least one connecting wire interconnected with, and extending from, the first loop; and (c) a second substantially closed loop of wire interconnected with the at least one connecting wire and configured to assume a shape lying substantially on the virtual cylinder at a position displaced from the first loop in a direction substantially parallel to an axis of the virtual cylinder.

According to a further feature of the present invention, the device structure is a filter structure for obstructing passage of particles of dimensions greater than a predefined value along the vessel.

There is also provided according to the teachings of the present invention, a method for reducing flow impedance through a vessel previously provided with an intravascular device including a device structure supported by a support structure, the method comprising: (a) detaching the device structure from the support structure; and (b) removing the device structure while leaving the support structure.

There is also provided according to the teachings of the present invention, a retrieval system for retrieving a temporarily deployed un-tethered intravascular device, the retrieval system comprising: (a) a crown connected to the un-tethered intravascular device, the crown including at least one projecting element; (b) a retrieval catheter having a distal end for insertion to a position close to the intravascular device the distal end having a longitudinal central axis; and (c) a retrieval device deployed within, and advanceable beyond, the retrieval catheter, the retrieval device including a plurality of wire portions, the plurality of wire portions being configured such that, when the retrieval device is advanced to extend beyond the distal end of the retrieval catheter, each of the wire portions opens into a substantially planar loop in a plane parallel to, and lying substantially on, the longitudinal central axis, the plane of each of the loops being rotated about the longitudinal central axis relative to the planes of others of the loops, such that, when the retrieval device is advanced beyond the distal end and moved towards the intravascular device, the crown passes between the wire portions so as to lie within at least one of the loops, and when the retrieval device is withdrawn, at least one of the wire portions is engagable on the at least one projecting element so as to catch the crown and to allow withdrawal of the intravascular device.

There is also provided according to the teachings of the present invention, an intravascular filter for minimally invasive deployment within a vessel so as to obstruct the passage of particles of dimensions greater than a predefined value through the vessel, the intravascular filter comprising at least one flexible elongated member configured to assume a spiral filter form including a plurality of turns of a spiral, wherein a spacing between portions of the flexible elongated member in adjacent turns is sufficiently small to form an obstacle to passage through the spiral filter form of particles having dimensions greater than the predefined value.

According to a further feature of the present invention, the spiral is implemented as a conical spiral.

According to a further feature of the present invention, the at least one flexible elongated member is attached to, or integrally formed with, a guidewire in such a manner that the intravascular filter can be drawn into a catheter by withdrawal of the guidewire.

According to a further feature of the present invention, there is also provided a retrieval catheter deployed around the guidewire for receiving the at least one flexible elongated member, the retrieval catheter having an internal channel of diameter at least equal to a diameter of at least three innermost turns of the spiral such that the at least three innermost turns of the spiral enter the retrieval catheter without being significantly straightened.

According to a further feature of the present invention, the spiral filter form includes at least two substantially co-axial spirals.

There is also provided according to the teachings of the present invention, a method for trapping and removing particles of dimensions greater than a predefined value carried by fluid flow through a vessel, the method comprising: (a) introducing a catheter into the vessel; (b) advancing from the catheter an intravascular filter including at least one flexible elongated member configured to assume within the vessel a spiral filter form including a plurality of turns of a spiral, wherein a spacing between portions of the flexible elongated member in adjacent turns of the spiral is sufficiently small to form an obstacle to passage through the spiral filter form of particles having dimensions greater than the predefined value; and (c) removing the intravascular filter together with particles trapped therewithin.

According to a further feature of the present invention, the spiral is implemented as a conical spiral.

According to a further feature of the present invention, the at least one flexible elongated member is attached to, or integrally formed with, a guidewire extending through the catheter.

According to a further feature of the present invention, the flexible elongated member is initially located within the catheter so as to be coextensive with a distal portion of the guidewire, the flexible elongated member being pulled out from the catheter by advancing of the guidewire beyond a distal end of the catheter.

BRIEF DESCRIPTION OF THE DRAWINGS

The invention is herein described, by way of example only, with reference to the accompanying drawings, wherein:

FIG. 12B illustrates the variation of tension in the wire of the device of FIG. 12A as it is withdrawn and catches on the intravascular device;

FIG. 12C illustrates various states of a book form of flexible wire formed around an object as tension is applied to the wire;

FIG. 12D illustrates a situation similar to FIG. 2C wherein the hook is restricted by internal walls of a catheter;

FIG. 15A is a schematic axial view of an intravascular filter including a spiral filter form, constructed and operative according to the teachings of the present invention;

FIG. 15B is a side view of the filter element of FIG. 15A;

FIG. 16A is a schematic cut-away side view showing the filter of FIG. 15A deployed within a vessel;

FIG. 16B is a schematic cut-away axial view showing the filter of FIG. 15A deployed within a vessel;

FIG. 26A is a schematic cut-away side view illustrating withdrawal into a catheter of a conical spiral filter form by a guidewire connected to it's center;

FIGS. 26B and 26C are views similar to FIG. 26A illustrating two stages of withdrawal of filter forms where cross-pieces and/or opposingly wound spirals resist inversion of the conical form;

DESCRIPTION OF THE PREFERRED EMBODIMENTS

The present invention relates to intravascular devices and, in particular, it concerns semi-retrievable intravascular devices and corresponding methods. The invention also relates to retrieval systems for retrieving intravascular devices, and filter structures for use in intravascular devices.

The principles and operation of devices and methods according to the present invention may be better understood with reference to the drawings and the accompanying description. More specifically, details of various semi-retrievable devices and the associated methods will first be described with reference to FIGS. 1-6. Then, with reference to FIGS. 7-14B, various preferred retrieval systems and the associated methods will be described. Finally, with reference to FIGS. 15A-29, various preferred intravascular filter structures will be described.

Parenthetically, it is important to note that, while each of the various aspects of the present invention may be used to advantage in combination with the other aspects, each is believed to also be of patentable significance when used alone with otherwise conventional systems and techniques. Thus, the semi-retrievable intravascular devices and methods may be implemented using filter structures other than those disclosed herein, and in the context of devices other than filters. Furthermore, the retrievable portion of the device may be retrieved by any suitable retrieval system and method, not limited to the systems described herein. Similarly, the retrieval systems described herein may be employed to retrieve both semi-retrievable and fully-retrievable devices of all types. Similarly the filter structures of the present invention may be used to advantage both as part of a guidewire tethered system (such as for carotid distal protection) and as part of an un-tethered retrievable, semi-retrievable or permanent intravascular device.

Semi-Retrievable Devices

Figure 1A:
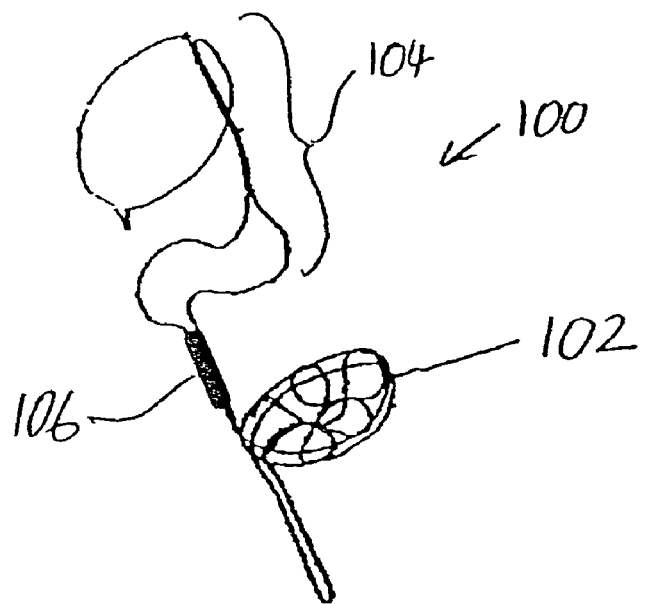
FIG. 1A is a schematic isometric view of a semi-retrievable intravascular filter, constructed and operative according to the teachings of the present invention, including a support platform and a filter structure interconnected by a releasable connector.

Referring now to the drawings, FIG. 1A illustrates a semi-retrievable or partially retrievable device, generally designated 100, constructed and operative according to the teachings of the present invention, for intravascular deployment. In general terms, this aspect of the invention relates to an intravascular device, exemplified here by an intravascular filter; wherein a first part 102 of the device which forms the primary flow impediment is selectively detachable from a second anchoring part 104 of the device so that first part 102 can be removed when no longer required while second part 104 remains permanently implanted.

By way of non-limiting example, the invention is here exemplified in the context, of a device including a filter and platform substantially as taught by unpublished co-pending, co-assigned PCT Patent Application No. PCT/IL02/00358. The structure described therein is modified by addition of a releasable connector 106, examples of which will be described below. Clearly, the filter structure may advantageously be replaced by one of the various filter structures described hereinbelow. Furthermore, as already stated, the principles of the present invention is equally applicable to a range of other devices as will be clear to one ordinarily skilled in the art. With regard to the support platform, here too the structure described in the aforementioned PCT application is believed to be particularly advantageous, but the teachings of the inventions may also be applied to a wide range of alternative platform structures As discussed above, when an intravascular device is left in place over extended periods of weeks or months, the endothelium tends to grow over portions of the device in contact with the vessel wall causing them to become permanently attached. In many cases, however, significant parts of the device have little or no contact with the vessel wall. This is clearly true for the operative part of a filter structure which is distributed across the width of the vessel. If all or most of the parts of the device positioned within the flow are removed from the device, the lumen of the vessel is left wide open with all remaining supporting and attaching structures substantially flush with the vessel wall. Thus, according to the teachings of the present invention, a flow impeding device such as a filter is built such that the primary flow impeding portions can be removed while leaving the support platform in place. This allows a device such as an IVC filter to be left in for months, or even years, and then effectively removed without significantly damaging the vessel wall to subsequently permit normal blood flow.

Figure 1B:
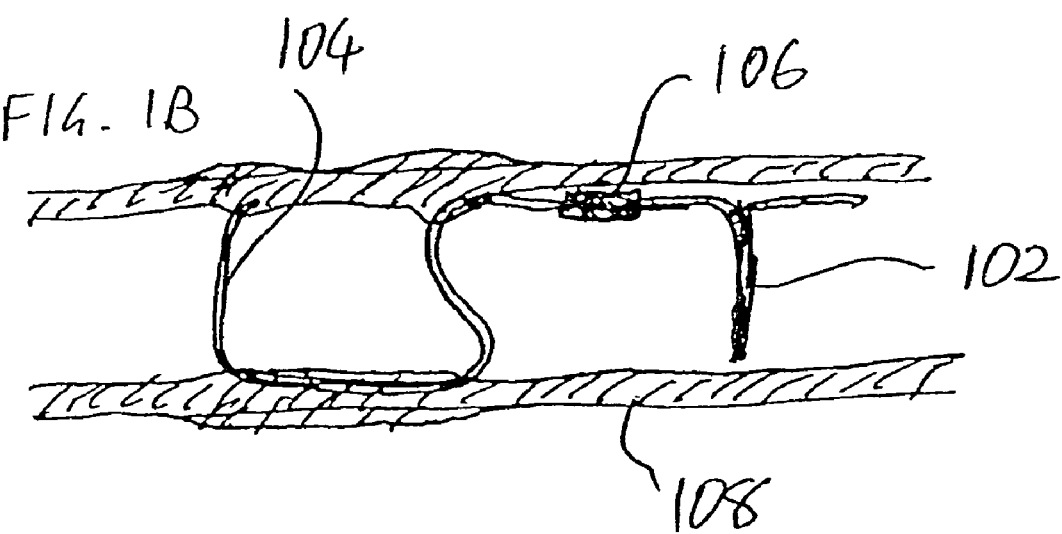
FIG. 1B is a schematic cut-away view of the semi-retrievable intravascular filter of FIG. 1A deployed within a vessel.
Figure 1C:
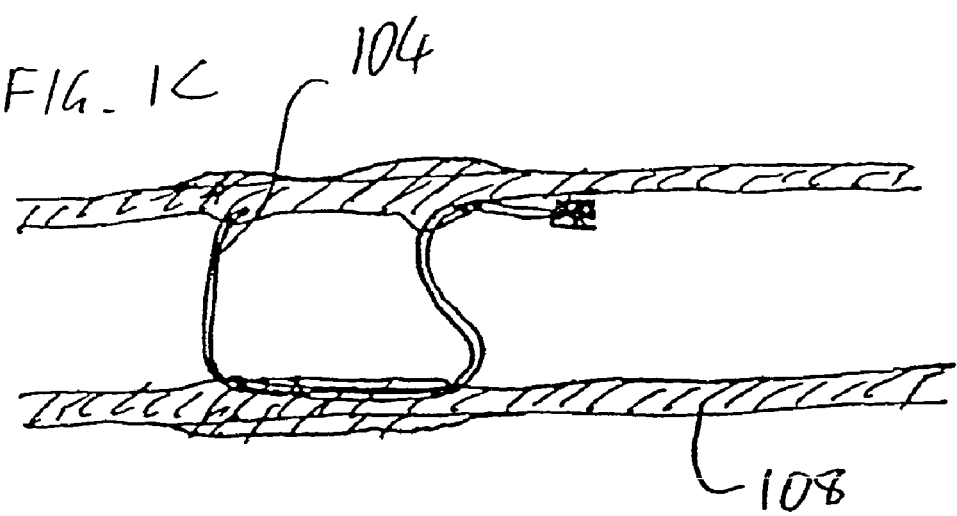
FIG. 1C is a view similar to FIG. 2B after removal of the filter structure.

Thus, in the example illustrated, FIG. 1B shows device 100 deployed within a vessel 108. In this state, first part 102 of the device performs its intended function, such as filtering solids from the flow through vessel 108. When this function is no longer required, connector 106 is disconnected and first part 102 is removed (by any suitable retrieval technique), leaving second part 104 embedded in the vessel wall (FIG. 1C). Since second part 104 is made up of loops and connecting portions which all lie substantially on a cylinder corresponding to the inner surface of the vessel, the remaining portion causes greatly reduced, and typically negligible, disturbance to flow through the vessel.

Clearly, this selectively detachable interconnection can be achieved in many different ways. The present invention, in its broad interpretation, is not particularly limited to any one type of interconnection. Examples include, but are not limited to, soldering, crimping, twisting together and winding or wrapping. The form of interconnection is preferably chosen to avoid, or at least minimize, degradation of the properties metal alloy (e.g. Nitinol) which is used. Optionally, the interconnection is configured such that a predefined amount of tension applied to the inner filter wire will cause the joint to open. The magnitude and/or direction of tension required to cause detachment is chosen to ensure that detachment does not occur inadvertently during normal operation of the device. Alternatively, mechanical locking may be used. By way of non-limiting but preferred examples, a few possible forms of interconnection will now be described.

One preferred group of implementations employs a connecting element (collar, bead, sleeve, winding etc.) which retains (grips or locks) both wires in its connected state, typically encircling them, and which allows separation of the wires under predefined conditions. The wires may be locked by friction, by performing the resilient wire into a shape which locks itself within the connecting element, or by any combination of these and other connecting techniques.

Figure 2A:
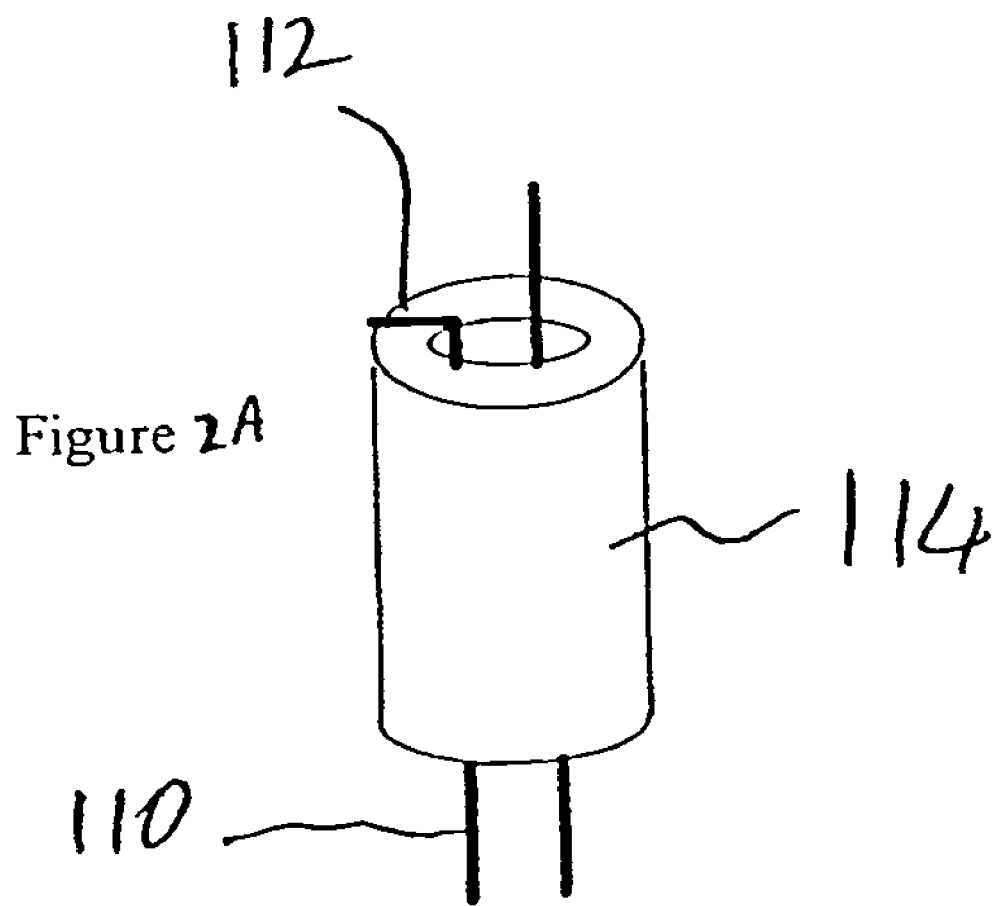
FIG. 2A is a schematic illustration of a first implementation of a releasable connector for use in the semi-retrievable intravascular filter of FIG. 1A.
Figure 2B:
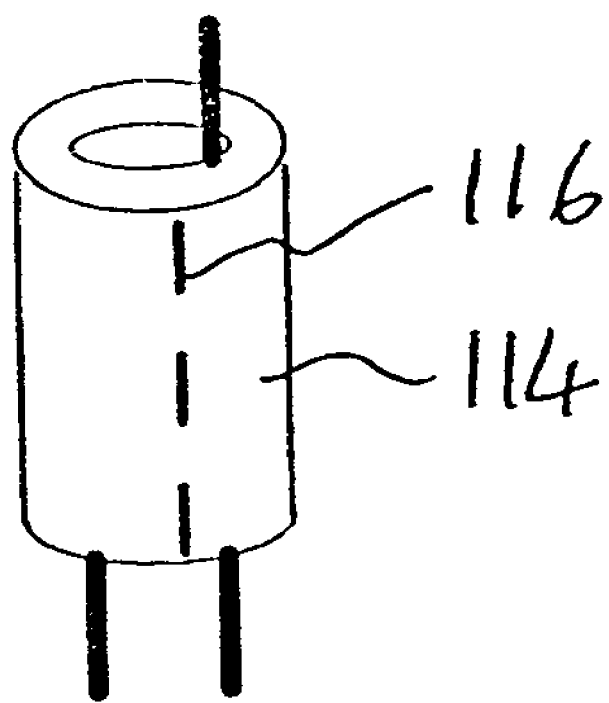
FIG. 2B is a schematic illustration of a second implementation of a releasable connector for use in the semi-retrievable intravascular filter of FIG. 1A.

By way of specific non-limiting examples, FIG. 2A shows schematically a connection in which one wire 110 is bent over at its end to form a small bend or hook 112 which tends to lock the wire within a collar 114. When a predetermined amount of tension is applied along wire 110, hook 112 becomes sufficiently deformed to allow the wire to slide out and detach. Alternatively the end of the wire may be embedded in the collar and retained only by frictional and/or adhesive forces, again allowing it to detach when sufficient tension is applied.

In a further set of implementations, the connecting element 114 may itself be configured to separate into two separate portions each of which remains attached to its respective wire. The region of separation may be defined by frangible connections or otherwise defined "weak areas" (dotted line 116 in FIG. 2B), providing a parting line which separates under the predefined conditions for detachment.

Figure 3:
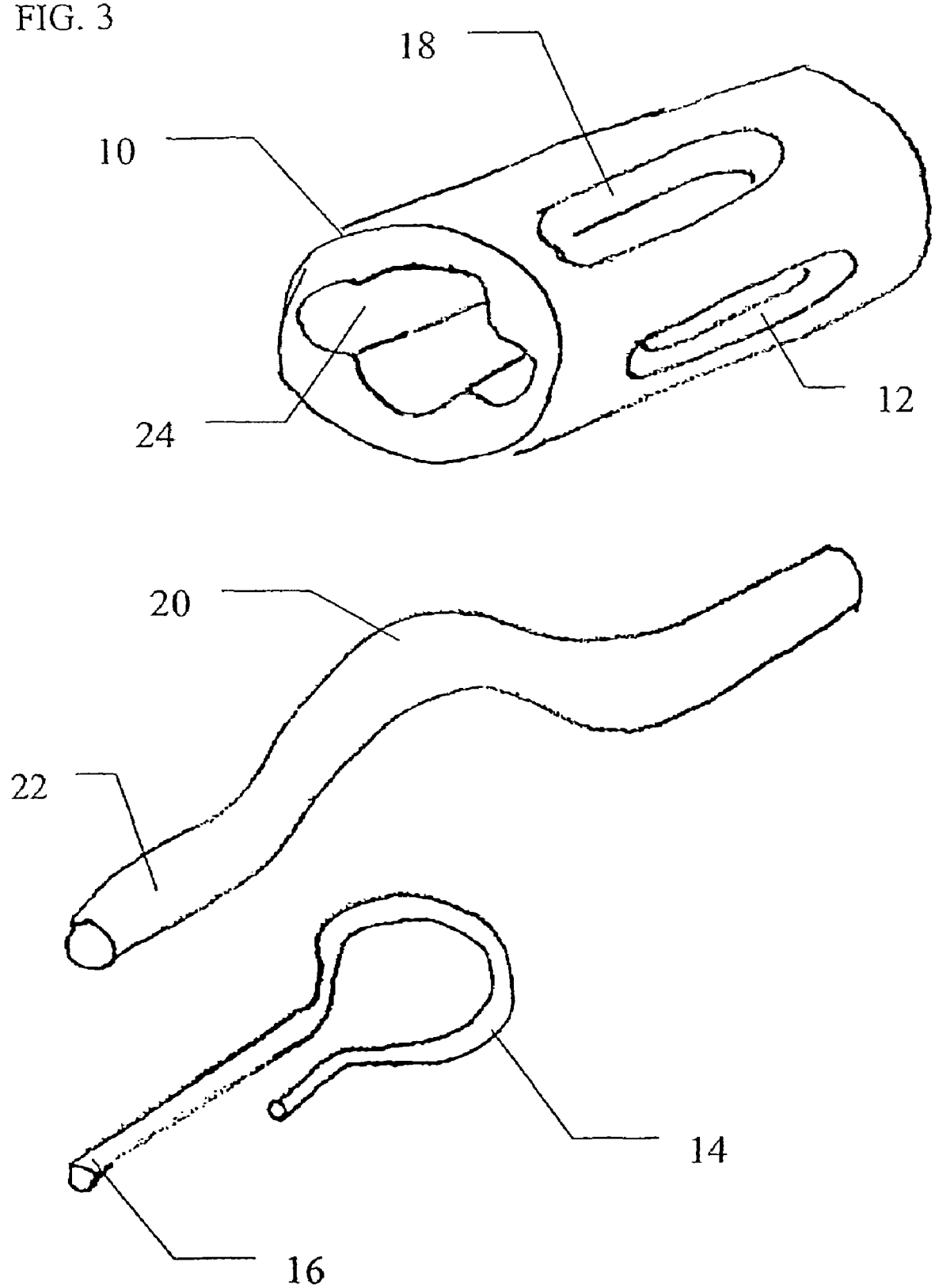
FIG. 3 is a disassembled isometric view of components of a third implementation of a releasable connector for use in the semi-retrievable intravascular filter of FIG. 1A.
Figure 4:
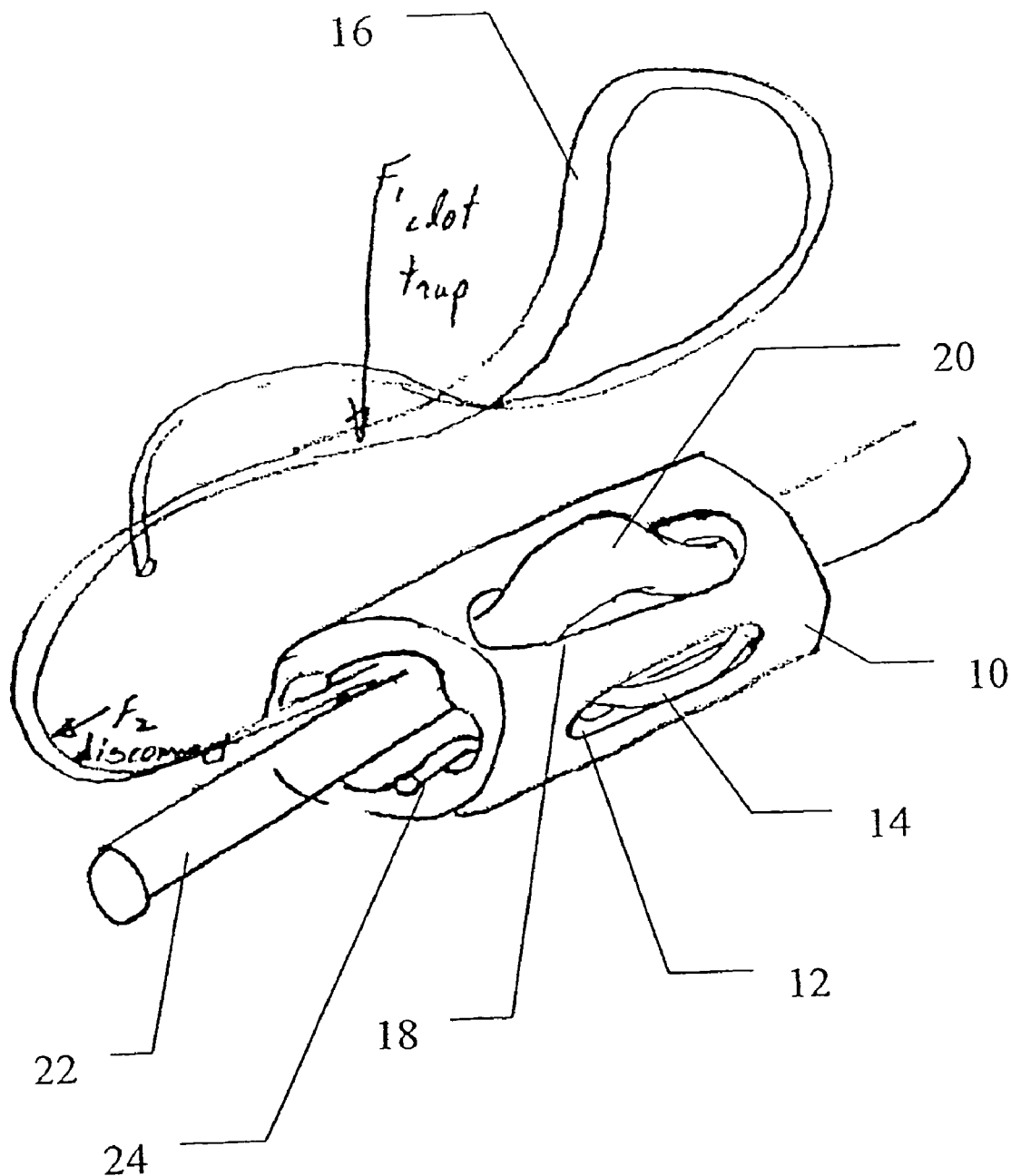
FIG. 4 is an isometric view of the releasable connector of FIG. 3 when assembled.

A further example employing the concept of resilient retention is presented in FIGS. 3 and 4, where the resilient retention is supplemented by a sequential locking configuration. FIG. 3 shows a collar 10 with a pair of lateral slots 12 (only one of which is visible) for receiving opposite portions of a spring loop 14 formed near the end of a first wire 16. An additional slot 18 in collar 10 receives a correspondingly shaped bent portion 20 of a second wire 22. The positions of the slots, the dimensions and shape of the wires and the shape of an internal channel 24 of collar 10 are preferably chosen such that, when both wires are inserted as shown in FIG. 4, a part of first wire 16 passes beneath the portion 20 of wire 22 which engages slot 18, thereby preventing straightening of wire 22 so as to positively lock the support wire in its engaged position. This arrangement, which may clearly be generalized to any situation where two wires are required to detach in a predefined sequence, ensures that the forces applied during detachment of the filter cannot inadvertently detach the collar from the second wire.

Retrieval is achieved by introducing a sheath into the relevant vein and then advancing to the level of the filter. A retrieval device, such as those described below, is then advanced. Once the retriever is attached to the filter wire, tension is applied until the wire becomes detached. The filter wire may then be removed into the sheath leaving the support platform attached to the IVC wall.

The tension to be applied to free the central filter wire is defined to be sufficiently small to avoid detaching the supporting rings from the vessel wall. Preferably, as an additional precaution against detachment from the IVC wall, the retrieval system sheath is pushed up against the outer wire while tension is applied to the filter wire. This creates a push-pull situation, ensuring that very little force acts on the supporting rings themselves relative to the vessel wall. Additionally, the retriever is preferably attached to the filter wire adjacent to the connection to the outer wire/collar, thereby localizing the applied forces as much as possible.

Figure 5:
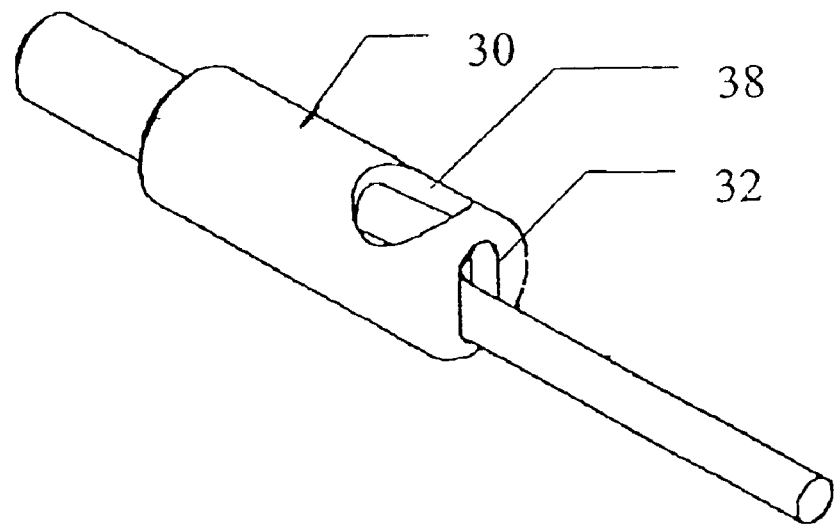
FIG. 5 is an isometric view of a fourth implementation of a releasable connector for use in the semi-retrievable intravascular filter of FIG. 1A.
Figure 6:
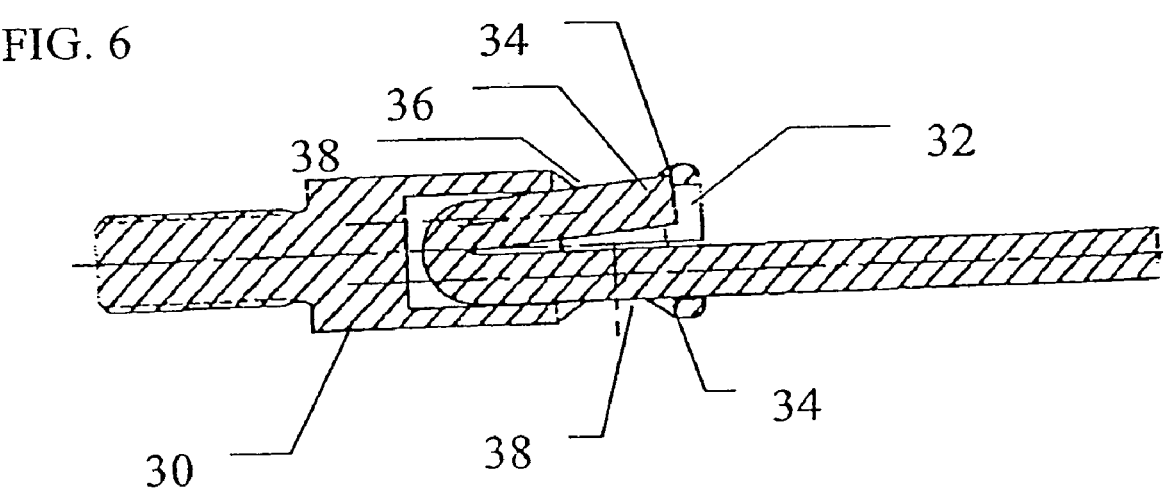
FIG. 6 is a longitudinal cross-sectional view through the releasable connector of FIG. 5.
Figure 7A:
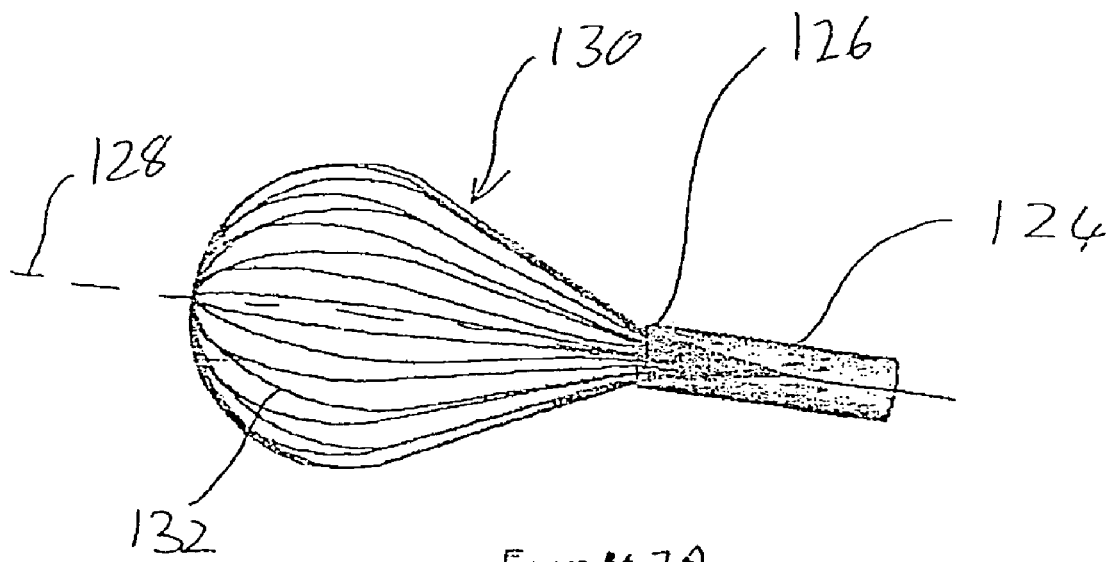
FIG. 7A is a schematic isometric view of a retrieval device for use in a system, constructed and operative according to the teachings of the present invention, for retrieving part or all of a temporarily deployed un-tethered intravascular device.
Figure 7B:
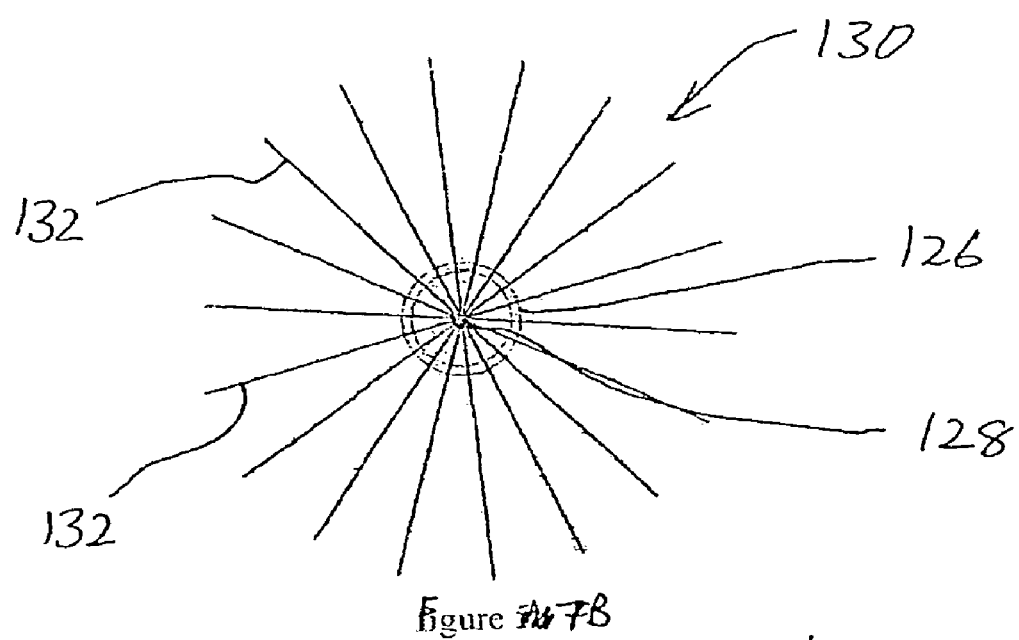
FIG. 7B is an axial view of the device of FIG. 7A.
Figure 8:
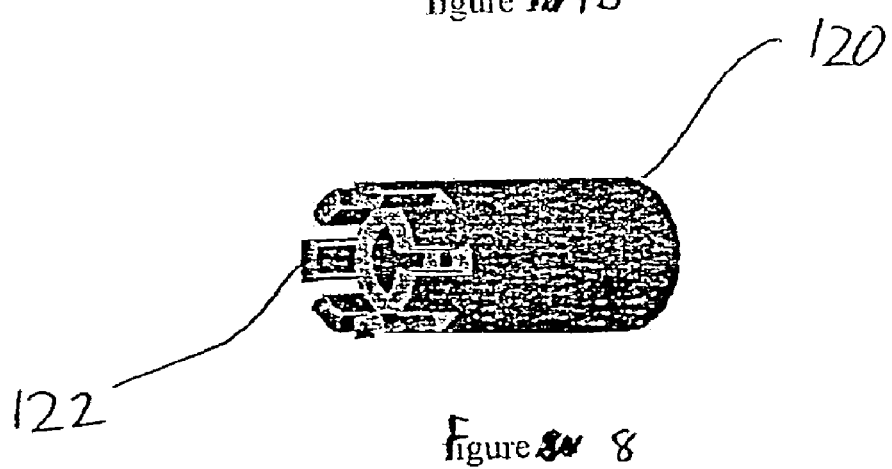
FIG. 8 is a schematic isometric view of a crown element for attachment to the un-tethered intravascular device to facilitate retrieval by the device of FIG. 7A.
Figure 9:
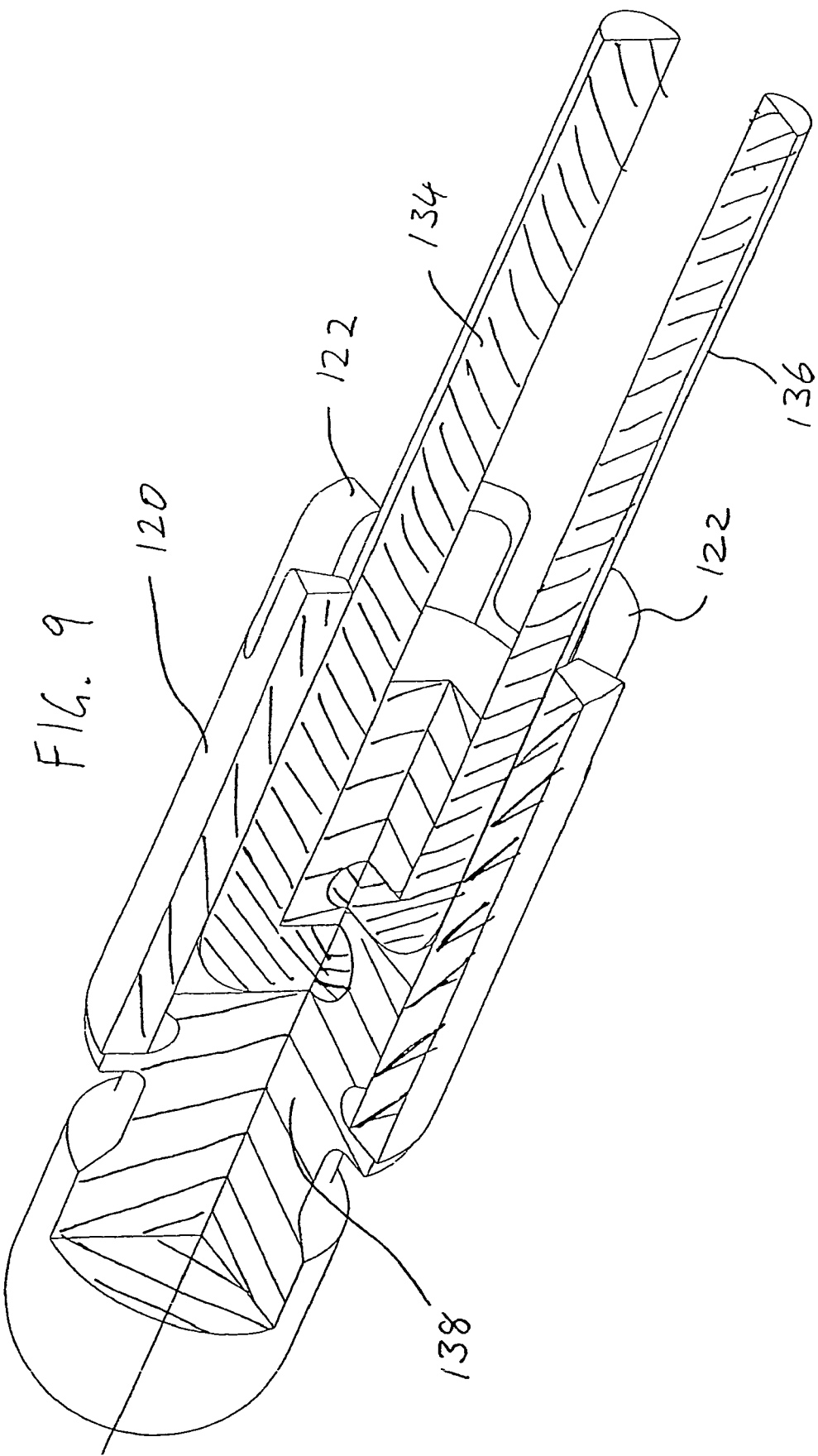
FIG. 9 is a partially cut-away isometric view of a wire connector assembly including the crown element of FIG. 8.
Figure 10:
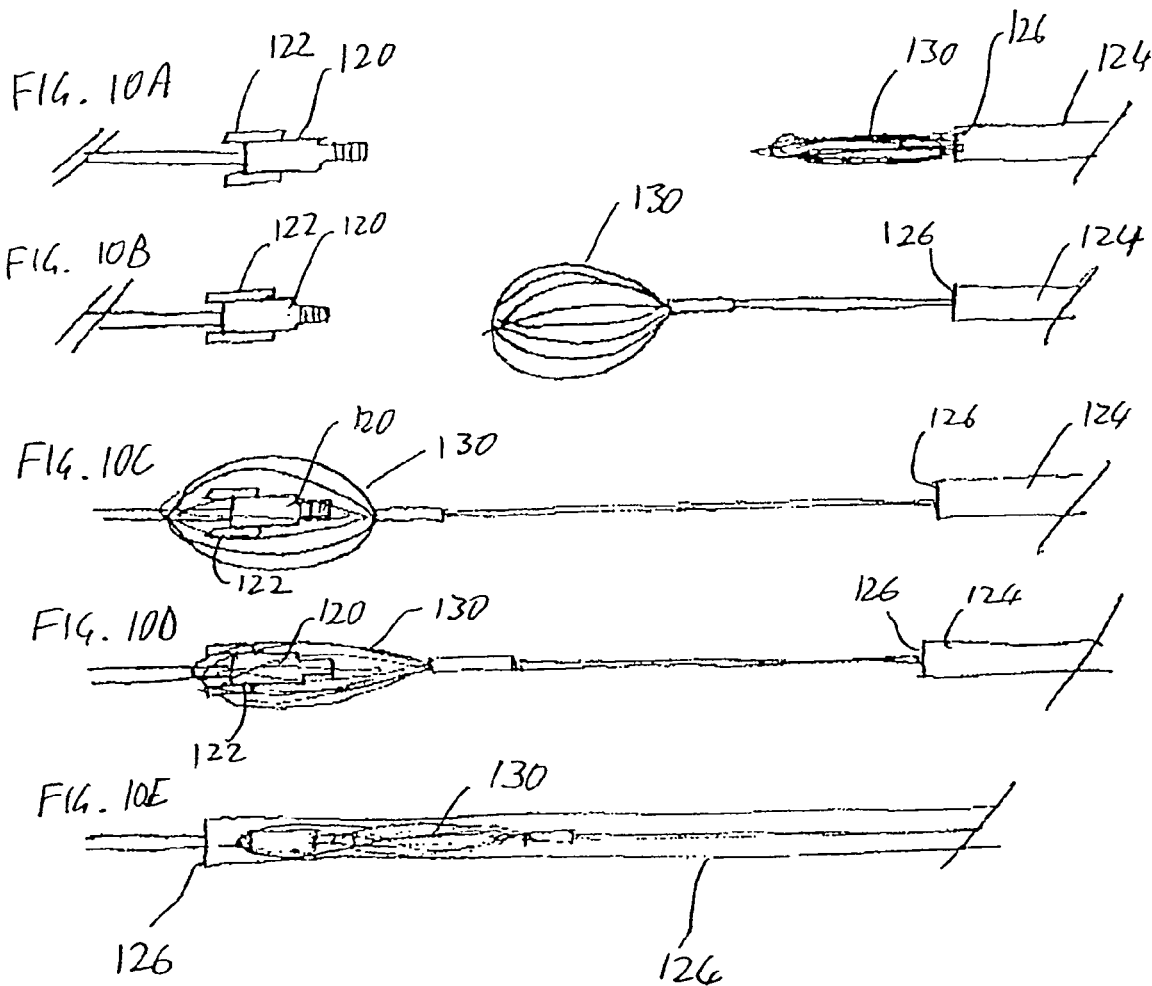
FIGS. 10A-10E are a sequence of schematic side views illustrating steps in the procedure of retrieving an intravascular device using the retrieval device of FIG. 7A.

Finally, with reference to FIGS. 5 and 6, there is shown a configuration and corresponding method for permanent or detachable connection of a wire, such as a Nitinol wire, without use of soldering, crimping, welding or other techniques which are known to compromise the properties of the wire. This configuration is believed to be of value in a wide range of applications not necessarily limited to the other features of the invention described herein.

Specifically, the connection configuration includes a connector housing 30 with a slot 32 which slightly exceeds the size of one diameter by two diameters of the wire. The housing is formed with one, and preferably two, lateral locking shoulders 34 which are located such that, when a folded over end 36 of the wire is inserted into housing 30 and passes shoulder 34, the end springs slightly open and becomes lodged against locking shoulder 34 so as to prevent retraction of the wire. The provision of two shoulders 34 renders the housing symmetrical such that the folded end of the wire can be inserted in an arbitrary orientation through slot 32.

Optionally, housing 30 may be provided with openings 38 as shown, adjacent to shoulders 34, so as to provide access to end 36. In this case, a suitable tool may be employed to apply inward force to the end 36 of the wire, thereby depressing it momentarily so as to allow it to be pulled out past shoulder 34. In an alternative implementation, housing 30 may be implemented without openings 38 to provide a permanent connection configuration.

Retrieval Systems

Turning now to FIGS. 7A-14B, various retrieval systems according to the teachings of the present invention will now be described. One particularly preferred implementation of a retrieval system is illustrated here with reference to FIGS. 7A-10E.

Thus, FIGS. 7A-10E show various parts of retrieval system, constructed and operative according to the teachings of the present invention, for retrieving a temporarily deployed un-tethered intravascular device, In general terms, the retrieval system includes a crown 120 (FIGS. 8 and 9) connected to the un-tethered intravascular device (not shown), the crown including a number of projecting elements 122. The retrieval system further includes a retrieval catheter 124 having a distal end 126 for insertion to a position close to the intravascular device, the distal end having a longitudinal central axis 128. Within catheter 124 is deployed a retrieval device 130, which is advanceable beyond retrieval catheter 124. Retrieval device 130 includes a plurality of wire portions 132 configured such that, when device 130 is advanced to extend beyond distal end 126 of retrieval catheter 124, each of wire portions 132 opens into a substantially planar loop in a plane parallel to, and lying substantially on, the longitudinal central axis. The plane of each of the loops is rotated about longitudinal central axis 128 relative to the planes of others of the loops, giving a structure resembling a miniature egg whisk.

Operation of the retrieval system is illustrated schematically in FIGS. 10A-10E. First, the retrieval catheter 124 containing the initially collapsed retrieval device 130 is introduced into the vessel close to the device to be retrieved (FIG. 10A). Retrieval device 130 is then advanced beyond distal end 126 so the device 130 assumes its open form (FIG. 10B). Device 130 is then advanced towards the intravascular device to be retrieved until crown 120 passes between wire portions 132 so as to lie within at least one of the loops (FIG. 10C). Then, retrieval device 130 is withdrawn slightly until at least one of the wire portions 132 engages on at least one projecting element 122 (FIG. 10D). The retrieval device 130 can then be withdrawn, or retrieval catheter 124 advanced as shown here in FIG. 10E, so as to draw crown 120 and hence the intravascular device into the retrieval catheter 124.

It should be appreciated that the structure described provides profound advantages compared to conventional techniques such as the use of a snare. Specifically, the use of multiple loops in rotated axial planes helps to approximately center the device within the vessel so that the practitioner does not typically need to perform any fine manipulation. Furthermore, depending upon the density of the wires as will be discussed below, the capturing process (FIGS. 10B-10D) may be an automatic result of advancing the catheter as the smooth end of crown slides between adjacent wire portions 132 while the "hooked" side prevents its escape from the bulb of the "egg whisk" form.

A further advantage of this implementation is that crown 120 tends to center itself under tension (FIG. 10D) to a position in which it is near axis 128 and generally aligned therewith. This alignment is further enhanced by collapsing of the "whisk" as it enters catheter 124, thereby tending to keep crown 120 aligned within the catheter. This avoids the sideways alignment typically resulting from use of a snare, thereby allowing the use of a catheter of inner diameter not much greater than the diameter of crown 120, and preferably of inner diameter smaller that the length of crown 120.

Retrieval device 130 preferably includes between 4 and 20 wire portions lying in planes separated by rotation through approximating to 180°/n where n is the number of wires. Generally, devices with 10-20 wires are highly effective for blind retrieval where the crown is caught on the first attempt, but render it difficult to un-hook the crown if the practitioner decides to interrupt the withdrawal procedure. At the other extreme, low numbers of loops facilitate controlled hooking and un-hooking of the crown by axial rotation of the device, but may be less effective at ensuring axial alignment of the crown within the "whisk" as it collapses during withdrawal. An optimal balance between these considerations for a wide range of applications is thought to be using between 6 and 10 wire portions.

It will be noted that element 120 described here as a "crown" may be implemented in many different forms to provide the required directional hooking function. The cylindrical form illustrated is considered particularly advantageous both for it's simplicity of manufacture and for its mechanical properties. The smooth round end of crown 120 tends to find its way easily between adjacent wire portions 132 independent of the direction of approach. The axially directed projections 122 ensure that crown 120 does not catch easily on body tissue or the like.

In the preferred implementation shown here, crown 120 advantageously performs a number of different functions. Specifically, crown 120 is additionally configured to form part of a connector for clamping at least two wires 134 and 136 from the un-tethered intravascular device in fixed relation. In this example, clamping of the wires is achieved by insertion of bent ends of the wires into channels formed in a plug 138 over which crown 120 fits snugly as a cylindrical collar. Plug 138 or crown 120 can optionally also provide an attachment configuration (such as a screw thread or the like, not shown) for initial attachment to a guide wire of a delivery system to facilitate initial deployment of the un-tethered intravascular device.

While the retrieval system described thus far is believed to be particularly effective, the present invention also provides a number of alternative retrieval mechanisms which is each believed to be patentable in its own right. For the sake of conciseness, these will now be described briefly with reference to FIGS. 11-14B.

Figure 11:
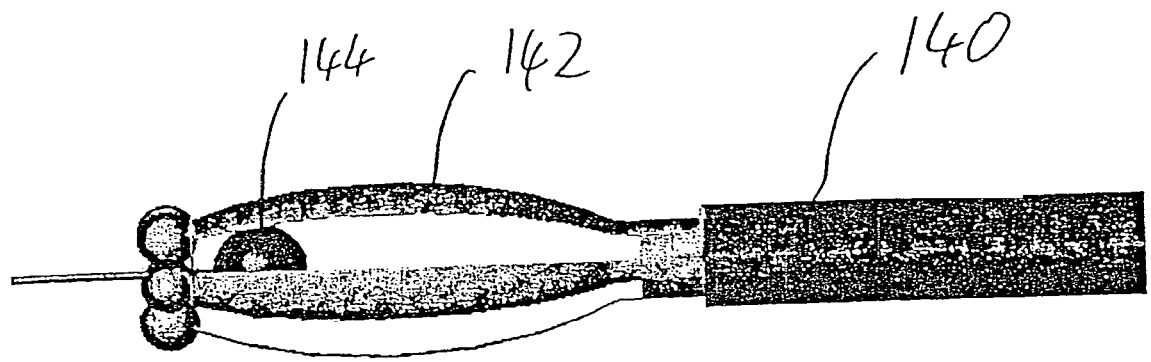
FIG. 11 is a schematic side view of an umbrella action retrieval device, constructed and operative according to the teachings of the present invention.
Figure 12A:
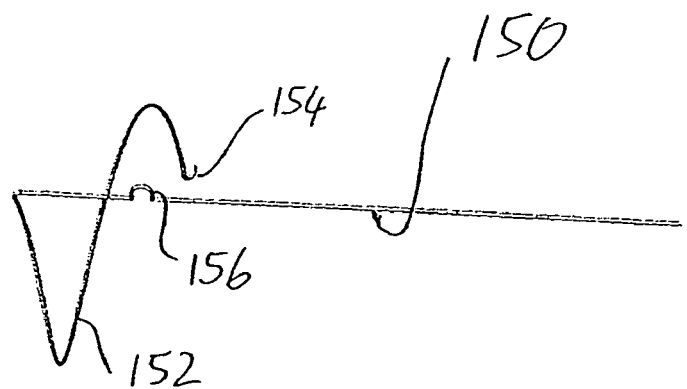
FIG. 12A is a schematic side view of an open-snare retrieval device, constructed and operative according to the teachings of the present invention.

FIG. 11 illustrates an "umbrella" concept in which a main extraction catheter tube 140 surrounds a mechanism of a number of extending fingers 142 arranged circumferentially around the longitudinal axis of the catheter and position in its distal end. The fingers expand resiliently in a radial direction once pushed out of the catheter. The fingers can contract inward to trap the small enlargement (e.g. round ball 144) at the proximal end of the intravascular device by sliding a second catheter tube (over tube) over the extraction tube. The fingers contract small enough to fit within the extraction catheter pulling the filter into the extraction catheter. At the end of each finger there is an enlargement which prevents the proximal enlargement from sliding out of the grabbing mechanism.

FIGS. 12A-12D illustrate a "single wire snare" concept. This employs a single wire 150 made of a shape memory alloy which, in its extended state is a straight wire, and in its relaxed state, and during deployment from the extraction catheter forms a backward loop 152 which acts as a snare to grab the a proximal enlargement of the intravascular device. The single wire is enclosed in the extraction catheter which is advanced up to the intravascular device. The wire has an end 154 which resembles a hook. It also has a bend 156 along its axis on which the hook should get caught during retrieval of the wire. The reason for the bend along the wire is as follows:

During the initial stage of wire retrieval, before the enlarged end of the intravascular device has been caught by the snare, minimum resistance force is applied against the retrieval of the wire into the extraction catheter. At the point where actual pulling has been applied to the device itself by the snare, the resistance force increases dramatically as shown below in FIG. 12B. If, at the point at which the resistance force increases dramatically, the hook at the end of the wire is still out of the extraction catheter, there is a possibility that the force applied through the wire will be high enough and will cause the hook to collapse and open to a straight wire (FIG. 12C)—a situation which will result in the failure of the extraction process. For that reason, there is a bend 156 in the wire that is designed to catch the hook 154 and guide it into the extraction catheter before the actual pulling of the intravascular device takes place. With the hook inside the catheter, the catheter constrains the hook from overturning and opening (see FIG. 12D).

Figure 13:
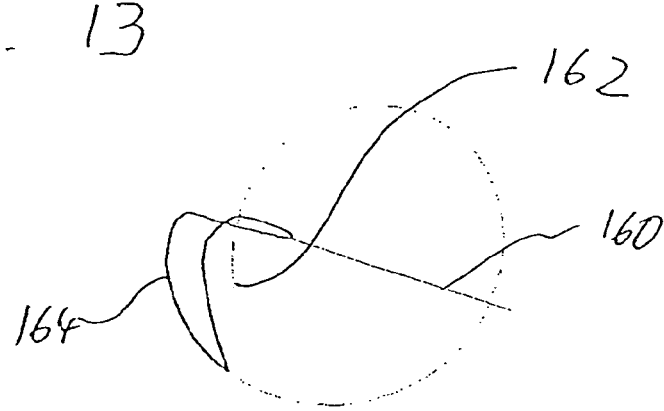
FIG. 13 is a schematic isometric view of an open-snare retrieval device, constructed and operative according to the teachings of the present invention, employing a trapping loop for trapping the loose end of the wire.

Turning now to FIG. 13, this illustrates a variation of the single wire snare including a loop. This retrieval device 160 is similar to the single wire snare 150 depicted above except that the loose end 162 of the wire here passes through a loop 164 formed in the wire. During withdrawal of the retrieval device into a catheter, loop 164 folds together, thereby locking end 162 to prevent opening of the snare. In this configuration, no additional bend is required to catch the loose end.

Figure 14A:
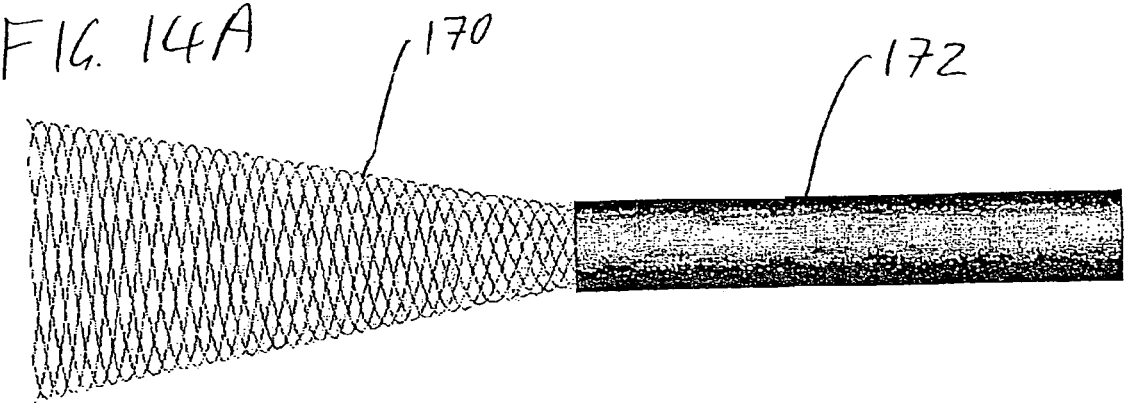
FIG. 14A is a schematic side view of a braided trap retrieval device, constructed and operative according to the teachings of the present invention.
Figure 14B:
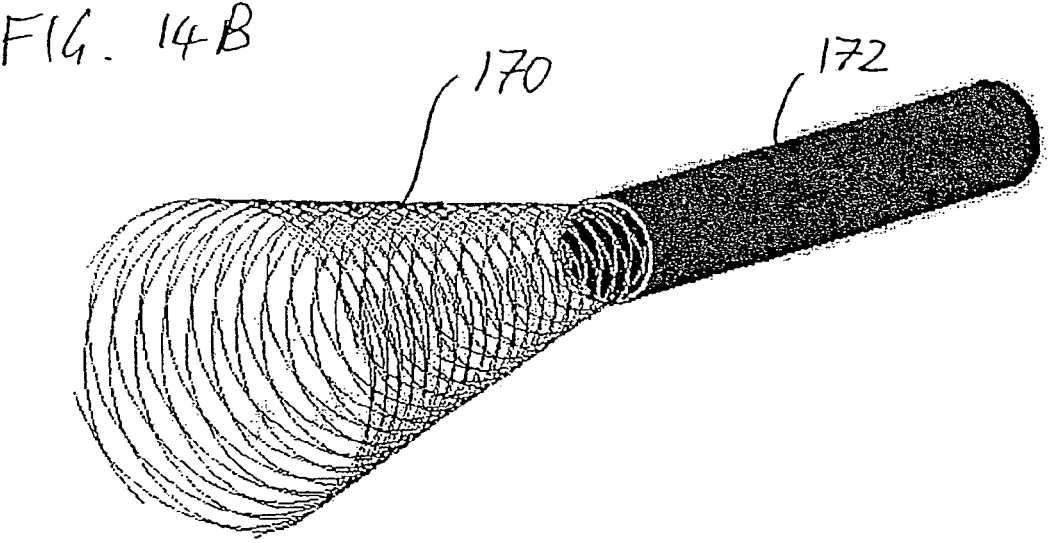
FIG. 14B is a schematic isometric view of the retrieval device of FIG. 14A.

Turning now to FIGS. 14A and 14B, there is illustrated a "braided trap" concept in which a braided tube 170 is made of Nitinol/Elgiloy/SS that is collapsed and attached at one end to a metal pusher (rod/tube). The braided tube diameter is about 12-18 mm. The number of wires, the diameter of the wires, the angle of braiding and the initial diameter are chosen to allow it to contract from its relaxed state to an internal diameter sufficiently small to trap the filter proximal end. When the free end of the braided tube exits the catheter, it regains its original diameter. By advancing and retracting the metal pusher, the free end of the braided tube goes out and into a catheter 172, and by doing so, its diameter at the free end changes from the relaxed diameter to the collapsed diameter. When the proximal end of the intravascular device is located somewhere along the internal diameter of the braided tube free end, it will get caught when the tube diameter is reduced to the collapsed state.

Intravascular Filter Structures

Turning now to FIGS. 15A-29, these illustrate various preferred implementations of an intravascular filter, constructed and operative according to the teachings of the present invention, for minimally invasive deployment within a vessel so as to obstruct the passage of particles of dimensions greater than a predefined value through the vessel. In general terms, the intravascular filter includes at least one flexible elongated member configured to assume a spiral filter form including a plurality of turns of a spiral, wherein a spacing between portions of the flexible elongated member in adjacent turns is sufficiently small to form an obstacle to passage through the spiral filter form of particles having dimensions greater than the predefined value.

The spiral, which typically includes at least five turns (although fewer may suffice for certain applications), is preferably implemented as a conical spiral, i.e., wherein the spiral is axially spread to generate an overall conical shape. Ideally, each turn of the spiral lies substantially on a virtual cone, although various practical implementations may vary considerably from this geometrical definition, for example, approximating more to a hemispherical or frustro-conical profile as viewed from the side. Preferably, the conical shape has an inclination θ to the axis of between about 10° and about 90°, and most preferably between about 30° and about 70°. This conical angle helps to concentrate any collected particulate material in the central region of the cone, thus facilitating effective removal of the material as will be described below.

In one set of preferred applications of the filter structures of the present invention, the elongated member forming the filter structure is attached to, or integrally formed with, a guidewire in such a manner that the intravascular filter can be drawn into a catheter by withdrawal of the guidewire. Various options for interconnection between the filter form and the guidewire will be discussed further below. The guidewire may be used as a guidewire for additional devices during performance of a medical procedure, making the filter suited for use as a distal protection device, for example, for use during procedures in the carotid artery.

Alternatively, the filter structures of the present invention may be used in un-tethered intravascular devices which are deployed for short-, medium-, or long-term use within a blood vessel or other vessel. In this case, the spiral may optionally be extended to provide a substantially helical outer portion to support the structure directly against the wall of the vessel. Alternatively, or additionally, the device may be supported by a distinct support platform. The latter option allows the filter to form part of a semi-retrievable device such as those described above.

Optionally, in order to facilitate effective removal of any accumulated particulate material, the intravascular filter may be retrieved using a retrieval catheter having an internal channel of diameter at least equal to the diameter of at least three innermost turns of the spiral. This allows a plurality of innermost turns of the spiral to enter the retrieval catheter as a group without being significantly straightened, thereby carrying with them any particulate material trapped therein. This procedure may optionally be further enhanced by use of momentary flow reversal, as is known in the art.

The retained intravascular filtering system may be introduced into a vessel through a tailored delivery system, for example a catheter, as a single complete structure. Within the catheter the retained intravascular filtering system is collapsed into a linear form. The retained intravascular filtering system is deployed within the vessel from the end of the catheter, and as it emanates, it is designed to reacquire its three-dimensional shape and expand within the bounds of the vessel's inner walls. The retained filtering system is further designed to remain attached to, or retained on, a guide wire that may be used simultaneously for additional purposes such as, for example, stenting and ballooning devices. The size of the filtering device relative to the vessel may be selectively arranged to occlude the complete lumen without exerting significant pressure on the vessel's inner walls, or the filtering device may lie within these dimensions.

The mechanisms for the filtering device to reacquire its three dimensional shape from its linear form within the tailored delivery system are preferably based upon properties of the material from which the device is constructed. The filtering device is ideally constructed from a material with appropriate shape memory and/or super-elastic properties. In particular shape memory properties enable the device to be stored in a deformed state until used, where a state change induced by the host environment through for example change in temperature will cause the device to assume its desired shape. Shape memory allows the device to be deployed through a tailored delivery means, where such means is designed to assume a very small profile compared to the device's overall desired operative shape, and thereby induce a minimized and fully reversible stress loading on the device's material. Similarly, super-elastic properties would allow gross deformation of the filtering device during deployment without compromising its ability to reassume the desired shape, and also permitting retrieval by similar or identical means. A suitable candidate material with these and other suitable properties is Nitinol, which is also relatively inert in living tissue, forms of super-wound stainless steel and shape memory polymers.

The filtering device is formed from smooth materials to avoid direct embolization on the surfaces of the filter. The filter may be fabricated in linear form from a single piece of wire, thereby avoiding joining mechanisms that may compromise the material properties. The wire is shaped and annealed to retain that form. The device may also be constructed from several individual pieces (wires), and only joined at a select set of points, to ensure the functional properties are reliable and to minimize the areas coming under stress, and joining mechanisms that do not compromise the material properties can be employed, such as crimping or a form of welding, for example by laser, or by use of mechanical connectors such as that described above with reference to FIGS. 5 and 6. Alternatively, the device may be constructed from sheet material and cut for example by an ablating laser. These fabrication methods individually or in combination may be used to construct the various forms of the device described herein.

The retained filtering system is preferably put in place in the vessel by a tailored delivery system. The filtering device can be collapsed and straightened longitudinally inside a catheter for delivery into the vessel. The catheter end is positioned inside the vessel at a desired point for deployment. The device is then pushed or pulled from the end of the catheter by suitable means such as the guide wire to which is may be attached and retained, such that the portion which emerges unfolds gradually as it is no longer restrained by the catheter's walls. As the device is deployed it adopts a transformation from a collapsed linear and longitudinal disposition into its operative desired orientation, and is retained in any desired position along the vessel by suitable positioning of the guide wire, and/or by direct contact with the vessel wall and/or by connection to a suitable un-tethered support platform.

The collapsed device is designed to fit inside a catheter of a size reasonable to the application, and to be smooth sided in order to slide freely within the catheter through potentially tortuous paths and overcome the inevitable resistance caused by its affinity to expand into its operative state. An ideal cross section for the device when collapsed would be circular and smaller than or closely matched to the catheter's inner dimensions. However, other cross-sectional designs could be chosen to suit particular applications.

At a suitable point, for example after completion of the operative procedure, the retained filtering system may be removed in entirety by collapsing it back into a linear form inside the tailored delivery system. The guide wire may be pulled back to withdraw the filtering device which collapses as it enters the tailored delivery system, either gradually or in a single step, or in a combination of these methods depending on the relative size of the filtering device to the tailored delivery system. By suitable choice of dimensions and by suitable application of the methods and devices described herein the particulate caught within the filtering device may be drawn back with it into the tailored delivery system and thereby safely exit the body.

Turning now to the structure of the filter structures of the present invention in more detail, FIGS. 15A and 15B show a preferred embodiment of re filtering device, generally designated 200. In an ideal form the filtering device has a conical spiral wire backbone shown from axial (FIG. 15A) and side (FIG. 15B) viewpoints. The spiral is ideally an Archimedean spiral, i.e., with a radius that increases linearly with increasing angle subtended from a defined origin. The Archimedean spiral is also drawn out into a cone by increasing the height linearly with increasing subtended angle. In this manner any line of radius drawn from the center or vertex along the surface of the containing cone will cross each turn of the wire at a constant radial increment. By tailoring the linear constants of height and radius to the subtended angle, the device thus formed may be used to filter all particulate that has a minimum diameter in excess of the radial increment. Other particulate with a smaller minimum diameter but some other dimensions exceeding this radial increment may also be filtered statistically depending on the orientation when encountering the filtering device. It will be readily understood that this filter form is highly efficient in that it avoids crossovers of the wire, thereby ensuring that each part of the wire contributes efficiently to the filtering effect. Furthermore, the conical shape helps to collect any particulate matter at its center, thereby facilitating subsequent reliable retrieval of the particulate matter. These and other advantages will become clearer from the further description below.

The number of turns and radial and height increments may be chosen freely, to suit the dimensions of the vessel, and to ensure a workable length of wire when in elongated form. Optionally, the Archimedean spiral may be started from points other than the origin, leaving a larger hole at the center for which filtering coverage is achieved by additional cross-piece mechanisms described later. Furthermore, those skilled in the art will appreciate that other well known forms of spiral such as logarithmic and parabolic may be employed alternatively or in combination, for example the spiral could begin Archimedean and then switch at a desired point to a parabolic relationship between radial increment and subtended angle. In practice, the device may be designed to any conical spiral form not necessarily with an exact continuous mathematical equation, the approximate shape being sufficient for the application.

FIGS. 16A and 16B show a preferred embodiment of the retained intravascular filtering system fully deployed in the vessel shown from the side and cross-sectional viewpoints, respectively. The conical spiral filtering device has been deployed through a tailored delivery system for example a catheter previously inserted into the vessel. The filtering device is retained on a guide wire and centers itself within the vessel as it deploys from a linear straightened form within the tailored delivery system to reassume its shaped memory form. The guide wire may be attached either at the vertex of the cone or at the edge of the base of the cone with or without a suitable bend in the guide wire to center it. The filtering device appreciably occludes a vessel's lumen to particulate above a certain selected size, although does not in any other way impede fluid flow. The filtering device retained on the guide wire need not exert any pressure on the inner sides of vessel to remain in situ, and furthermore does not have to occlude the lumen fully where particulate flow may be appreciably contained within the central portion of the vessel. Alternatively, the filtering device may be designed to exert a small amount of pressure as it expands within the vessel in order to keep the guide wire in place except where pushed or pulled deliberately. In addition to retaining the filtering device the guide wire is available for sliding other instruments involved in the operable procedure through the tailored delivery system into the vessel in order to work upstream in fluid terms of the filtering device without the chance of particulate that may be released from the procedure passing beyond and damaging vital tissues. In this manner, particulate is caught within the filtering device. For example stents and/or balloons may be slid into position to perform angioplasty on the carotid artery.

Figure 19:
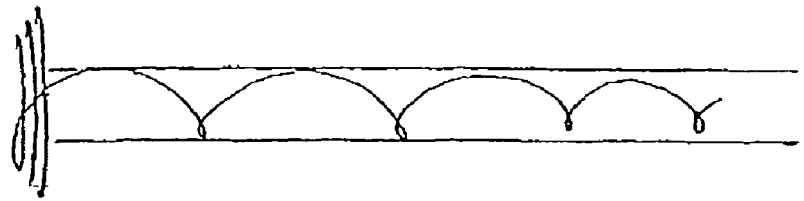
FIG. 19 is a schematic side cut-away view showing the filter of FIG. 15A tethered to, and pushed out from a catheter by, a guide wire during deployment, the spiral filter form being deployed from the outside inwards.
Figure 18:
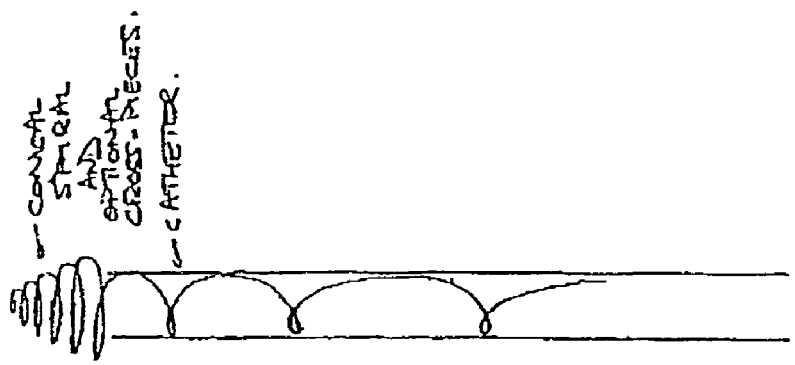
FIG. 18 is a schematic side cut-away view showing the filter of FIG. 15A tethered to, and pushed out from a catheter by, a guide wire during deployment, the spiral filter form being deployed from the center outwards.
Figure 17:
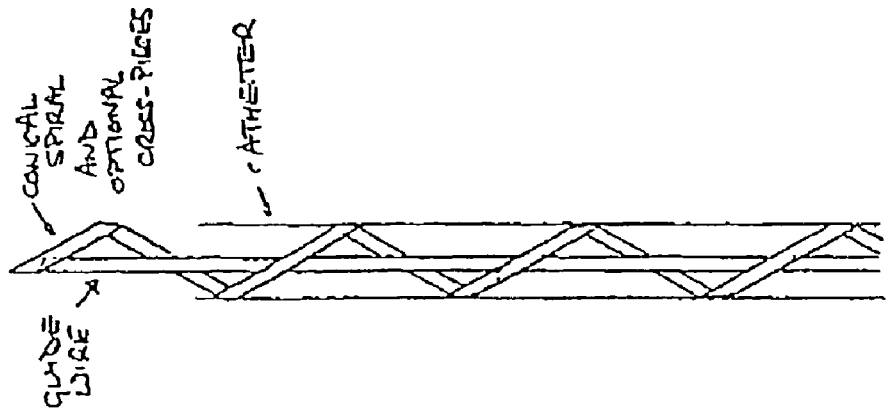
FIG. 17 is a schematic side cut-away view showing the filter of FIG. 15A tethered to, and pulled out from a catheter by, a guide wire during deployment.

FIGS. 17-19 illustrate various options for deployment of the intravascular filtering systems of the present invention. In FIG. 17, the filtering device is collapsed into an appreciably straightened form and pulled by the guide wire attached to the notional cone's vertex. The guide wire is pushed from outside the body until the filtering device has reached the desired position, and if necessary the catheter may be repeatedly slid back and forth to release any remaining length of the filtering device into the vessel, each stroke allowing more of the conical spiral shape to be reassumed. This implementation with the interconnection between the guidewire and the filter emerging first has advantages that the angle between the guidewire and the gradually forming conical spiral is well defined from the outset.

FIG. 18 depicts an alternative arrangement in which the guide wire is attached at the base of the notional cone of the filtering device and is used to push the filtering device through the catheter. The filtering device then deploys in its desired position as it emanates from the end of the catheter. The filtering device with the arrangements of FIGS. 17 and 18 may also include crosspieces described further in the discussion of FIGS. 20A and 20B below.

FIG. 19 shows a further option in which the guidewire is attached to the vertex of the notional cone of the filtering device, but the filtering device is deployed in reverse direction, the base forming first with the vertex deploying last. Inside the catheter, the device may be fully or only partially collapsed into a longitudinal linear form as suits the application allowing the catheter to be freely chosen for the sake of the size of stent and/or balloon and other devices, and also chosen to allow retention of particulate in the filtering device on retraction as per the discussion of FIGS. 25A-26C below.

Figure 20A:
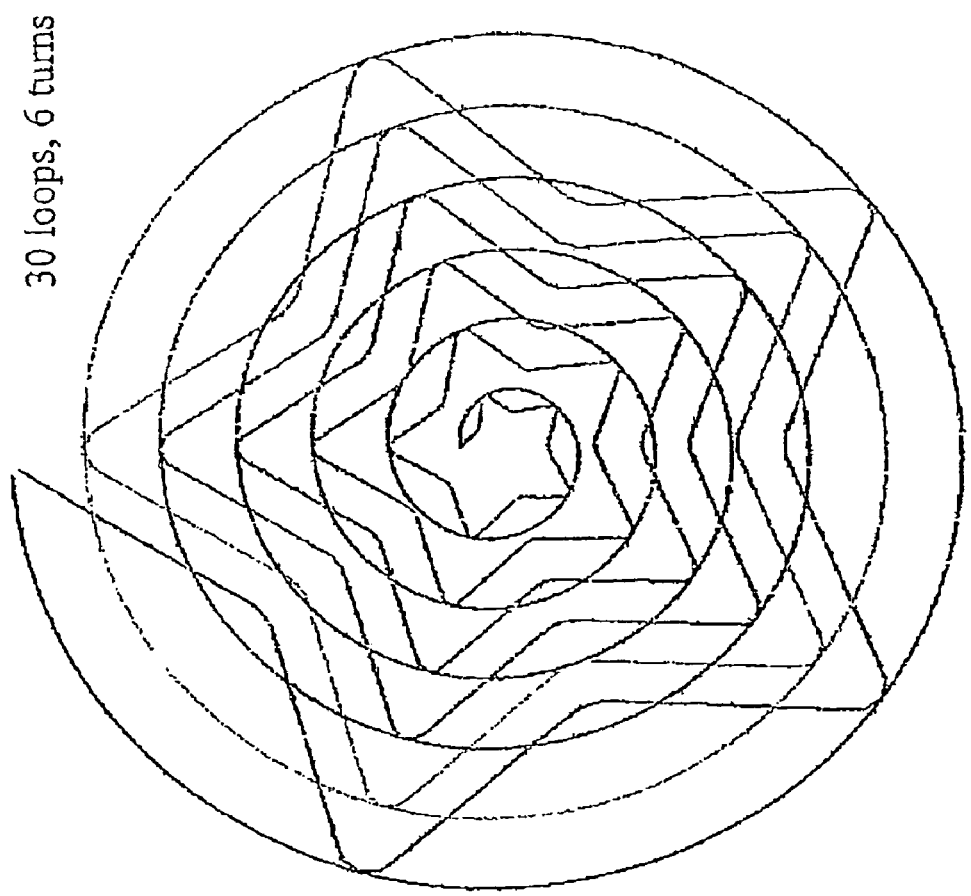
FIG. 20A is a schematic axial view of a filter form similar to that of FIG. 15A with addition of angularly periodic cross-pieces to provide dimensional support and extra filtering capability.
Figure 20B:
FIG. 20B is a schematic isometric view of the filter form of FIG. 20A.
Figure 21:
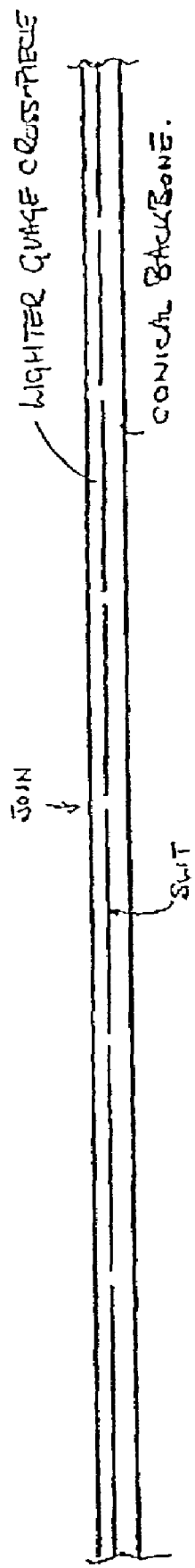
FIG. 21 is a schematic plan view of the filter form of FIG. 20A in straightened form prior to deployment, with the cross-pieces attached to the spiral backbone.

FIGS. 20A and 20B show an optional variant of the filtering device shown from axial and side viewpoints, respectively, with optional crosspieces with equal angular frequency, added to provide dimensional support and extra filtering capability. The crosspieces are formed in a manner similar to that described in co-assigned, co-pending PCT patent application no. PCT/IL01/00636. The crosspieces are selected to support the dimensions of the deployed conical spiral backbone and filter to ensure evenness of for over its wire's length. The crosspieces are formed from a continuous second wire of shape memory and/or super elastic properties that may be crimped or welded to the conical backbone wire. Alternatively the crosspieces and conical backbone may be formed from the same wire or ribbon or sheet material by cutting slits, for example by an ablating laser, to separate crosspieces and backbone where necessary and then shaped accordingly as shown in FIG. 21. Each crosspiece joins the backbone where they meet in the diagram, the length of the crosspiece between joins is appreciably equal in length to the backbone between the same points. The number of crosspieces may be chosen freely and widely. In the example shown in FIGS. 20A and 20B, the filter has 30 such crosspieces for six turns of the backbone. In this case, the crosspieces have an even angular frequency about the center. In this configuration, the crosspieces are designed to improve the spiral shape memory of the device when in situ, and also can provide-support of turns of the spiral above the ones to which they are attached such that under pressure from the flow of fluid in the vessel the conical spiral height is maintained or compressed to better retain particulate. The angular frequency may be also chosen to increase or decrease as a function of the radius. For example, in FIG. 27, the angular frequency increases as a function of reducing radius, which ensures that the crosspieces remain relatively larger towards the center of the spiral. A further function of the crosspieces is that their size may be chosen to supplement the filtering capability of the backbone. The crosspieces need not continue over the entire length of the backbone, depending on the function required of them in any given application.

Figure 22B:
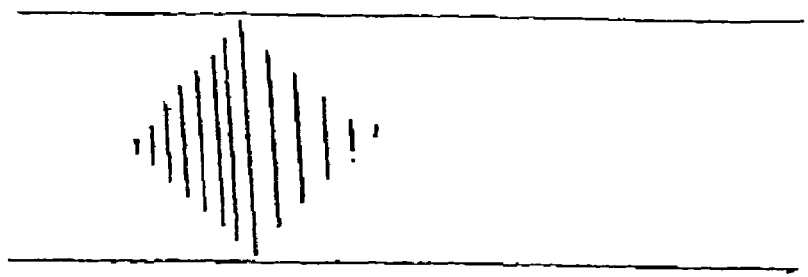
FIGS. 22A and 22B are schematic cut-away side views illustrating further optional variations of the filter form of FIG. 15A where two conical spiral filter elements are combined, one within the other and in inverted form, respectively, for greater filtering and particulate retention.
Figure 22A:
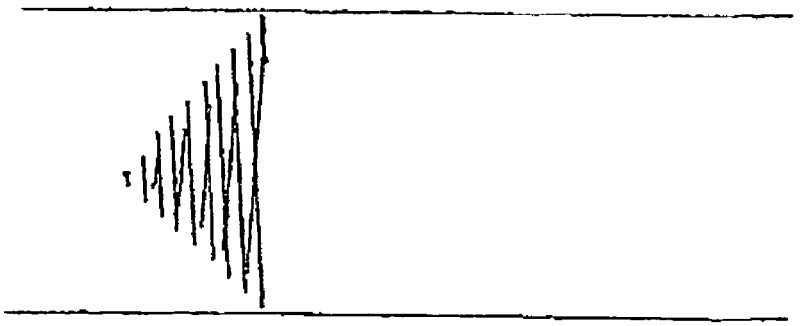

FIGS. 22A-24 show further optional variations of the filtering device using two joined conical spiral filters for greater filtering capability and particulate retention. In FIG. 22A, the two conical spiral filters are one inside the other and shown to be joined at the base of the notional cones thus formed. The guide wire may be joined at the vertex of the outer cone in which case the entire filtering device is pulled through the tailored delivery system, the outer cone forming first in an identical fashion to FIG. 17, and the inner cone forming second within the first as the catheter is withdrawn to and fro as necessary in a manner similar to that shown in FIG. 19. The guide wire may be joined alternatively at the vertex of the inner cone in which case the filtering device is deployed by being pushed from the catheter, the outer cone forming first in a manner similar to FIG. 18, and the inner cone forming second in a manner similar to FIG. 19. A further optional arrangement for attachment of the guidewire is at the base of both outer and inner cones. In the latter case, the two spirals are deployed and form simultaneously by being pushed from the catheter in a manner similar to that shown in FIG. 18. This arrangement of outer and inner cones could equally be joined at the vertex in which case the guide wire may be conveniently attached at the base of the inner cone and the filtering device deployed from the catheter by being pushed by the guide wire, the outer cone forming first appreciably as shown FIG. 19, and the inner cone forming subsequently appreciably as shown in FIG. 18. The dual advantage of the inner cone is to support the outer cone and assist in filtering to relieve some of the requirement of uniformity of the spiral dimensions over it's each wire's length. The inner cone may optionally include crosspieces for further support or filtering capability as described for the single cone above.

In FIG. 22B, one conical spiral filter is inverted with respect to the other conical spiral and they are joined at the bases of the notional cones thus formed. The guide wire may be attached to the vertex of the upper cone and the filtering device deployed by being pulled from the catheter appreciably as shown in FIG. 17. Alternatively, the guide may be joined at the vertex of the lower inverted cone and the filtering device deployed by being pushed from the catheter appreciably as shown in FIG. 18. Those skilled in the art will appreciate that the form of the dual cone in FIG. 22B may be alternatively appreciably spherical, as if a spiral on the surface of a ball. The spacing between successive turns of the spiral would be chosen and potentially varied across the surface to provide the desired filtering capability. Those skilled in the art will appreciate that either or both cones may optionally include crosspieces for further support or filtering capability as described for the single cone above.

Figure 24:
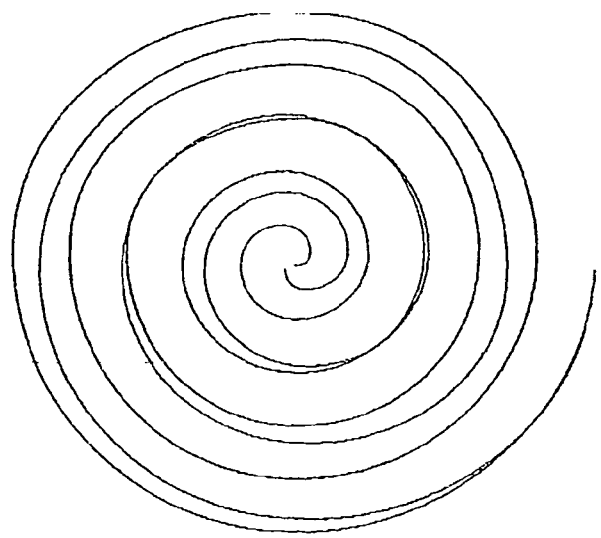
FIG. 24 is an axial view of the filter of FIG. 22A implemented with two spiral filter forms with the same winding directions.
Figure 23:
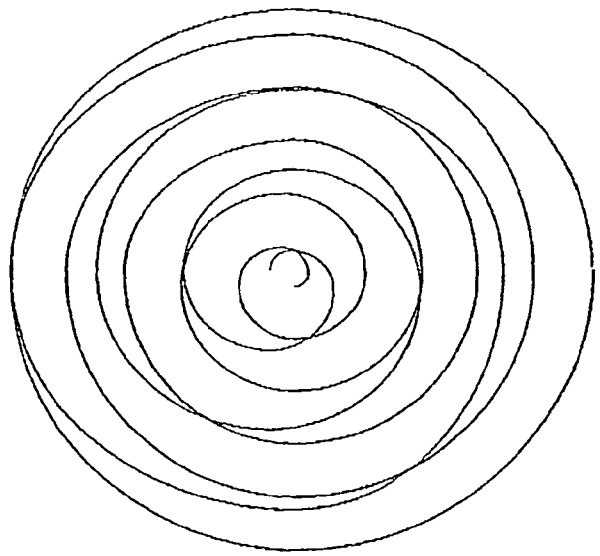
FIG. 23 is an axial view of the filter of FIG. 22A implemented with two spiral filter forms with opposite winding directions.

FIGS. 23 and 24 shows two options for implementing the variations of FIGS. 22A and 22B as viewed from an axial viewpoint. Specifically, the two cones, either inner and outer or inverted, maybe in co-wound form with continuous and non-reversed winding about a notional central axis, or alternatively, the direction of winding may be reversed. Thus, in FIG. 23, the two spirals may be implemented as a single long wire which extends from an outermost common loop spirally inwards in both a clockwise and an anticlockwise direction. On the other hand, in FIG. 24, the two spirals may be viewed as a folded wire, or two wires joined, at an outer extreme, both of which spiral inwards anticlockwise. Particularly in the case of FIG. 24, the two conical spirals are desirably chosen to be Archimedean spirals with different radial ratios between turns. Those skilled in the art will appreciate that the spirals may optionally be logarithmic or parabolic. The inner or lower inverted conical spiral is preferentially selected to have a larger spacing between successive turns of the spiral than the outer or upper inverted conical spiral. This allows the former to filter particulate of greater minimum diameter than the latter conical spiral with respect to fluid flow. Particulate of different sizes are stopped by each filter which helps ensure that there is less chance of clumping together and blocking fluid flow. Additionally, having smaller particulate trapped between the two conical spirals in both arrangements aids retention of the particulate on retraction from the body (FIGS. 25A-26C).

The dual conical spiral arrangements of FIGS. 22A and 22B may be formed from a single length of wire with shape memory and/or super-elastic properties. It may also be form from two discs, each conical spiral being cut out from a disc by laser ablation for example, and the discs or conical spirals joined according to the arrangements described above.

Figure 25A:
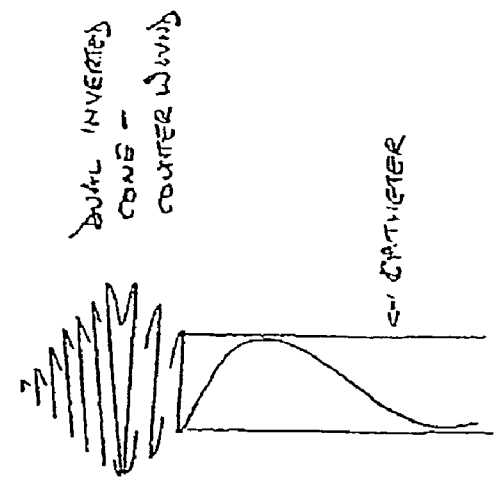
FIGS. 25A-25C are schematic cut-away side views illustrating withdrawal into a catheter of single conical spiral, co-wound inverted cone double spiral, and counter-wound inverted cone double spiral, filter forms, respectively.

Turning now to FIGS. 25A-25E, these show the retraction of the preferred embodiment and all variants of the retained intravascular filtering system into a tailored delivery system where the guide wire is attached to the base of the filtering device. In FIG. 25A, a single conical spiral is pulled from its base back into a catheter. The catheter may have the end cut-away in the form shown in FIG. 25D. Such an arrangement helps to unwind the conical spiral gradually and without greatly separating the successive turns to ensure the particulate caught within the filtering device are also withdrawn into the catheter. The size of the catheter is preferentially chosen to be larger than the spacing between successive turns of the spiral such that the last central turns may be withdrawn in their appreciably conical spiral form, and thereby retain and withdraw the particulate from the body. It may also be beneficial to reverse fluid flow while undergoing this retraction procedure by creating negative pressure within the catheter, and thereby assist further in the safe withdrawal of particulate. This single conical spiral may include the optional crosspieces described above.

Figure 25B:
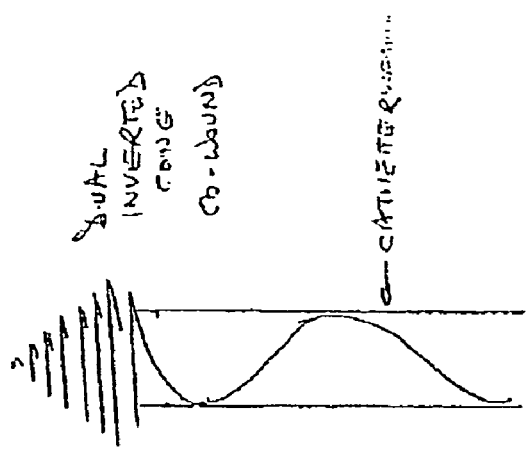
Figure 25C:
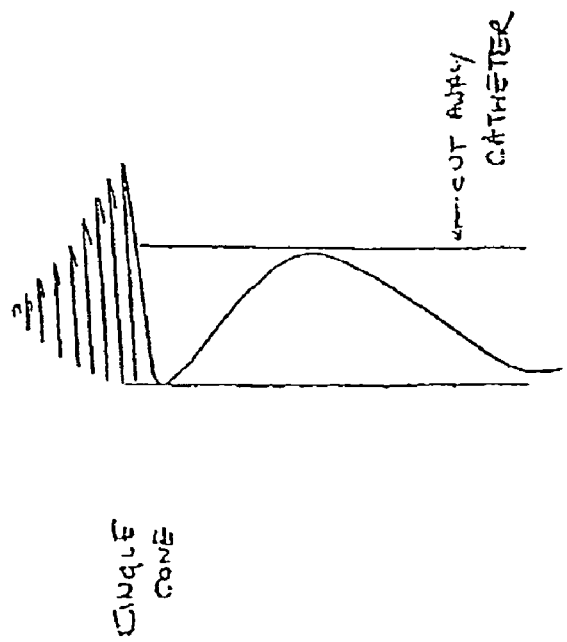
Figure 25D:
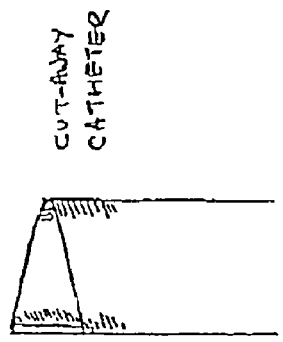
FIG. 25D is a schematic side view of a cut-away catheter configured for facilitating withdrawal of certain filter forms of the present invention.

FIGS. 25B and 25C show the retraction of the dual inverted conical spiral filtering device with co-wound and counter-wound conical spirals respectively. The guide wire is used to pull the filtering device against the end of the catheter and successively unwind the turns, any particulate being withdrawn inside the catheter or caught in the upper cone. The upper cone unwinds appreciably as described for the single cone, and the size of the catheter may be chosen preferentially to ensure that the last central turns of the upper conical spiral are withdrawn in their appreciably conical spiral form, and thereby retain and withdraw the particulate from the body. The upper and or the lower conical spirals may optionally include crosspieces.

Figure 25E:
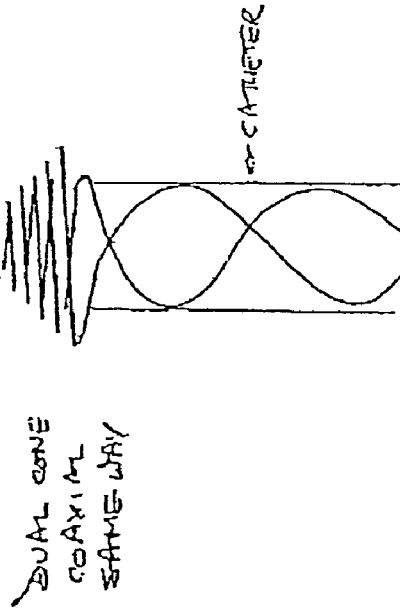
FIG. 25E is a schematic cut-away side view illustrating withdrawal into a catheter of a double spiral filter form according to FIGS. 22A and 24.

FIG. 25E shows the retraction of the dual inner and outer conical spiral arrangement. The guide wire is attached to the base of both cones and used to pull them into the catheter, the conical spirals unwinding together and withdrawing appreciably as described for the single cone. Where the guide wire is attached to the vertex of the inner cone then this inner cone will be inverted and pulled back first in a similar arrangement to FIG. 26A which shows the retraction of a single cone without crosspieces. As the inner cone retraction is almost completed the arrangement will be largely as depicted in FIG. 25B. Where the two cones are joined at their vertices, the guide wire is attached to the base of the inner cone, which is withdrawn first appreciably as shown in FIG. 25A, with the outer cone withdrawn thereafter appreciably as shown in FIG. 26A. The inner cone in such an arrangement may optionally include crosspieces and be withdrawn in this same manner.

FIGS. 26A-26C show the retraction of the preferred embodiment and all variants of the retained intravascular filtering system into a tailored delivery system with a guide wire attached to the distal apex of the filtering device. FIG. 26A shows the retraction of a single conical spiral without crosspieces. The guidewire is attached to the vertex and pulls the center of the cone first. The size of the catheter is preferentially chosen to be larger than the spacing between successive turns of the spiral such that three or more central turns may be withdrawn in their appreciably conical spiral form, and thereby retain and withdraw the particulate from the body.

FIGS. 26B and 26C show the retraction of a single cone with crosspieces or a dual inverted cone with crosspieces in the upper cone. With the guide wire attached to the upper vertex the filtering device is pulled back against the mouth of the catheter, and the crosspieces support the turns above the ones to which they are joined such that the height of the filtering device is compressed against them. As the filtering device is pulled further by the guide wire the crosspieces cave in to form a funneled guide and the upper cone is successively inverted and withdrawn into the catheter. The size of the catheter is preferentially chosen to be larger than the spacing between successive turns of the spiral such that most, if not all of the filtering device may be withdrawn in a compacted form, and thereby retain and withdraw the particulate from the body. Alternatively, once the stage shown in the second diagram has been reached, the catheter and the filtering device may be withdrawn from the body as a unit, the filtering device becoming quite rigid when compacted against the crosspieces and thereby fully retaining all the particulate. Such a scheme can also be applied to the other arrangements of filtering device and guide wire described above.

Figure 28:
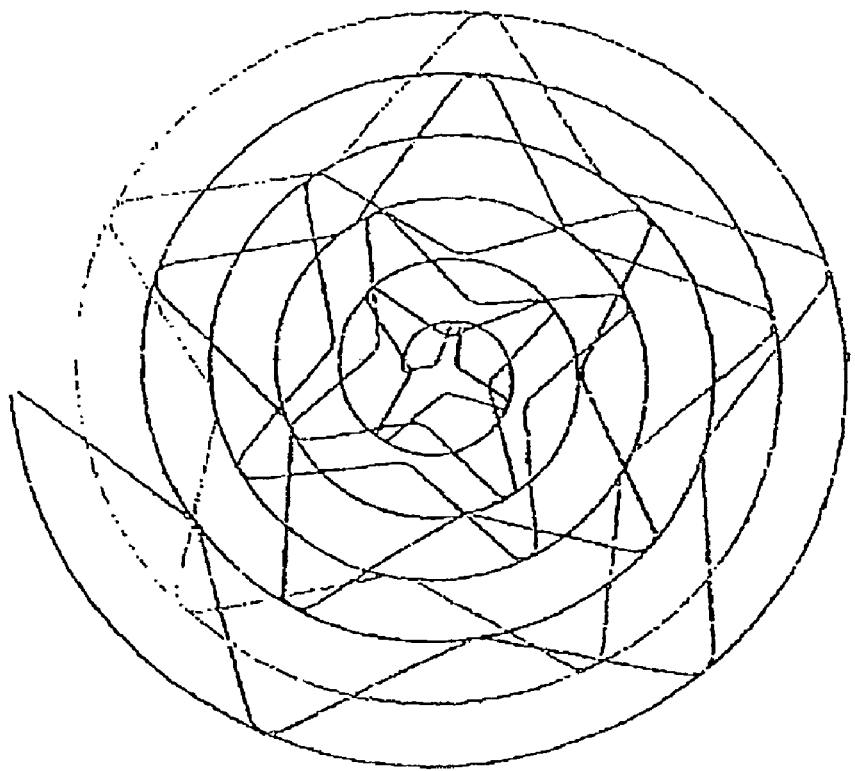
FIGS. 27 and 28 are schematic axial views of filter forms similar to that of FIG. 15A with addition of variable angular period cross-pieces with differing ratios of cross-piece loops to total turns of the spiral.
Figure 27:
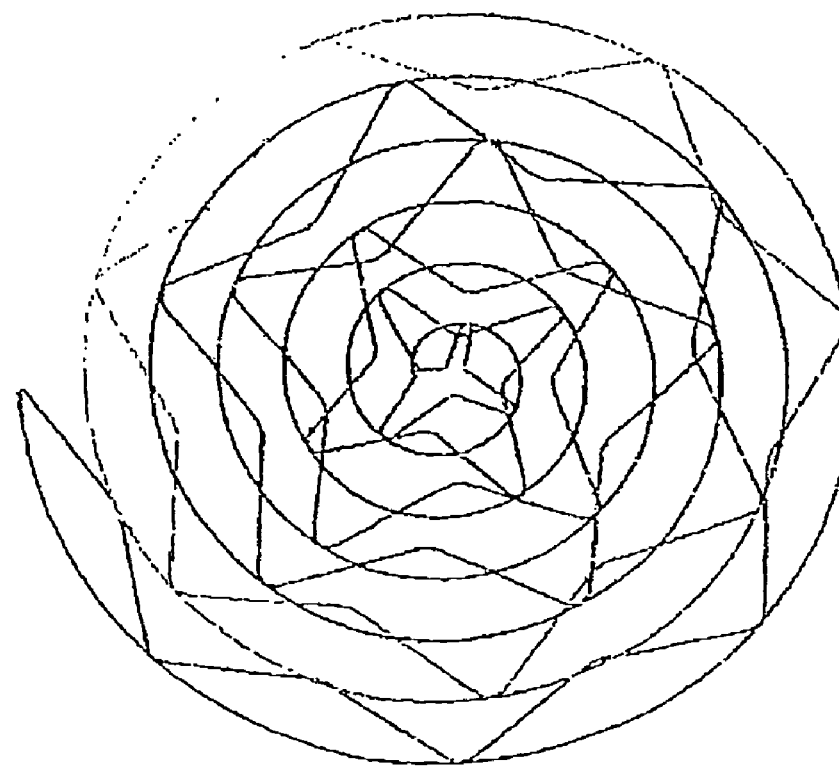

FIGS. 27 and 28 show from an axial viewpoint examples of a filter device with crosspieces of increasing angular frequency from center to periphery. Such an arrangement uses the crosspieces for support and to provide more uniform filtering capability. In FIG. 27, the ratio between successive crosspieces is 97%. This has the beneficial result of having more crosspieces the larger the radius of the spiral turn. This ensures that the crosspieces always overlap one previous inner turn. In FIG. 28, the ratio between successive crosspieces is 98%. This ensures that the crosspieces overlap almost regularly two previous inner turns. Those skilled in the art will appreciate that the ratio between successive turns need not be constant and linear and in the crosspieces could be individually selected and designed to best suit the spiral form of the backbone with any degree of overlap. A defined mathematical arrangement where used may assist in simplifying the construction of the filtering device.

Figure 29:
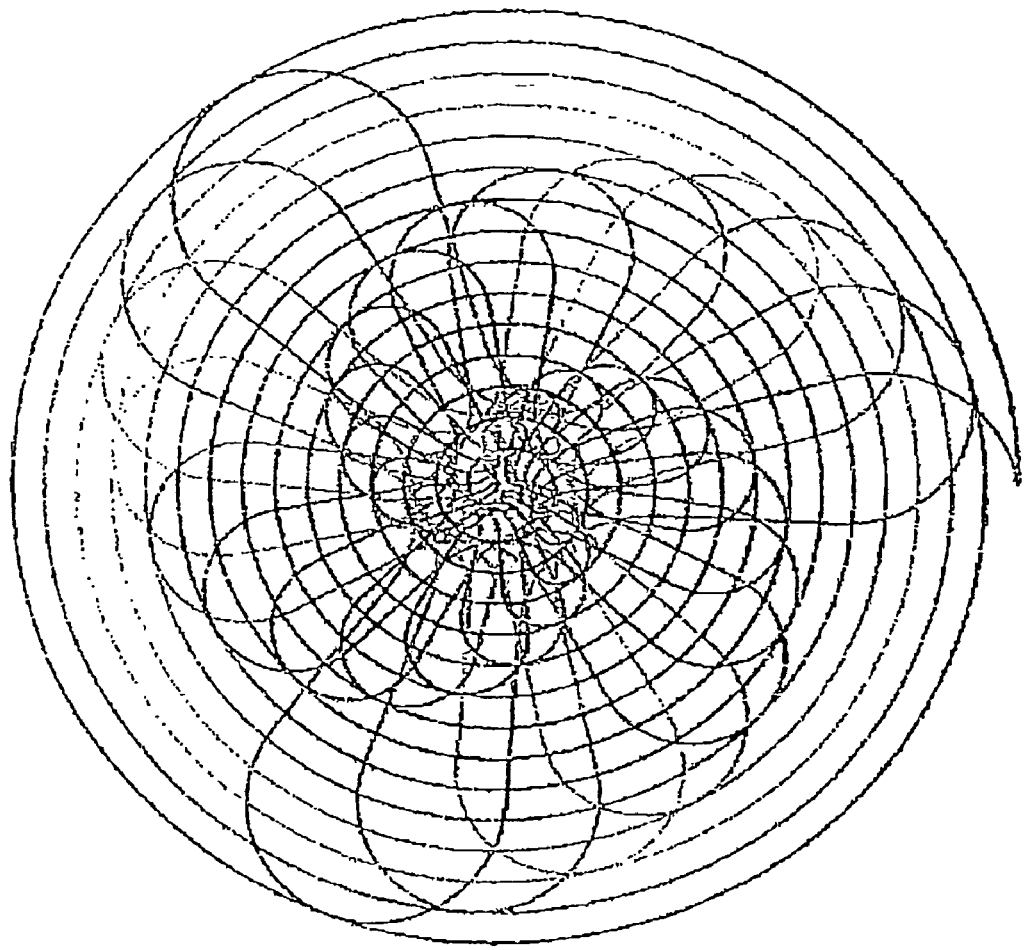
FIG. 29 shows is a schematic axial view of a filter form similar to that of FIG. 15A with addition of cross-pieces with a constant angular period for dimensional stability.

Finally, FIG. 29 illustrates an example of a filter to fit a 6 mm vessel such as is typical of the size of the carotid artery in the human adult. The implementation illustrated here shows an enlarged filtering device of approximately 6 mm diameter to filter particulate of 200 micron minimum diameter. The crosspieces of equal angular frequency contribute to dimensional stability of the structure.

It will be appreciated that the above descriptions are intended only to serve as examples, and that many other embodiments are possible within the spirit and the scope of the present invention.

What is claimed is:

1. A retrieval system in combination with an un-tethered intravascular device, the combination comprising:
   (a) a hookable element connected to the un-tethered intravascular device, said hookable element including a threaded portion for temporary interconnection with a delivery system, and at least one projection projecting towards the un-tethered intravascular device;
   (b) a retrieval catheter having a distal end for insertion to a position close to the intravascular device, said distal end having a longitudinal central axis; and
   (c) a retrieval device deployed within, and advanceable beyond, said retrieval catheter, said retrieval device including a plurality of wire portions, said plurality of wire portions being configured such that, when said retrieval device is advanced to extend beyond said distal end of said retrieval catheter, each of said wire portions opens into a substantially planar loop in a plane parallel to, and lying substantially on, said longitudinal central axis, said plane of each of said loops being rotated about said longitudinal central axis relative to said planes of others of said loops, such that, when said retrieval device is advanced beyond said distal end and moved towards the intravascular device, said hookable element passes between said wire portions so as to lie within at least one of said loops, and when said retrieval device is withdrawn, at least one of said wire portions is engageable on said at least one projection so as to catch said hookable element and to allow withdrawal of the intravascular device.

2. The retrieval system of claim 1, wherein said retrieval device includes a number n of said wire portions, where $4 \leq n \leq 20$, and wherein said planes are separated by angles which approximate to multiples 180°/n.

3. The retrieval system of claim 2, wherein $6 \leq n \leq 10$.

4. The retrieval system of claim 1, wherein said hookable element is additionally configured as a connector for clamping at least two wires from the un-tethered intravascular device in fixed relation.

5. The retrieval system of claim 1, wherein said hookable element has a substantially cylindrical external surface.

6. The retrieval system of claim 1, wherein said wire portions are mechanically unconnected at their distal extremities.

7. The retrieval system of claim 6, wherein each of said loops lies in a plane rotated relative to the plane of two others of said loops by no more than about 30 degrees.

8. The retrieval system of claim 6, wherein each of said loops has a smooth arcuate form at its distal extremity.

* * * * *